United States Patent
Fram

(10) Patent No.: US 9,852,272 B1
(45) Date of Patent: Dec. 26, 2017

(54) AUTOMATED REPORT GENERATION

(71) Applicant: D.R. Systems, Inc., San Diego, CA (US)

(72) Inventor: Evan K. Fram, Paradise Valley, AZ (US)

(73) Assignee: D.R. SYSTEMS, INC., San Diego, CA (US)

( * ) Notice: Subject to any disclaimer, the term of this patent is extended or adjusted under 35 U.S.C. 154(b) by 315 days.

(21) Appl. No.: 14/863,068

(22) Filed: Sep. 23, 2015

Related U.S. Application Data

(63) Continuation of application No. 13/530,754, filed on Jun. 22, 2012, now Pat. No. 9,177,110.

(Continued)

(51) Int. Cl.
*G06F 17/30* (2006.01)
*G06F 19/00* (2011.01)
(Continued)

(52) U.S. Cl.
CPC ........ *G06F 19/3487* (2013.01); *G06F 19/321* (2013.01); *G06T 7/0012* (2013.01);
(Continued)

(58) Field of Classification Search
CPC .................................................. G06F 19/3487
(Continued)

(56) References Cited

U.S. PATENT DOCUMENTS 6,347,329 B1 * 2/2002 Evans ................... G06F 19/322
  705/2
7,793,217 B1 * 9/2010 Kim ..................... G06F 19/3425
  715/255

(Continued)

FOREIGN PATENT DOCUMENTS

EP  1451734 A2  9/2004
EP  2130167 A1  12/2009

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

(Continued)

*Primary Examiner* — Mahesh Dwivedi
(74) *Attorney, Agent, or Firm* — Knobbe, Martens, Olson & Bear, LLP

(57) ABSTRACT

Provided herein are various systems and methods for improved report interaction and generation. A computing system receives selection of an exam for display on a display device, either from a user or as automatically determined by a computing device. The computing system may then determine an exam characteristic associated with the exam, such as an exam type. A data structure storing associations between exam characteristics and respective report packages, each of the report packages comprising a parent report and one or more child reports, may be accessed in order to select a report package associated with the determined exam characteristic. The child reports of the selected report package, which are configured to receive input from a user of the computing system that is usable in automatically generating content of the parent report of the selected report package, may be selectively displayed on the one or more displays.

20 Claims, 27 Drawing Sheets

Related U.S. Application Data

(60) Provisional application No. 61/500,896, filed on Jun. 24, 2011.

(51) Int. Cl.
*G06T 7/00* (2017.01)
*G06T 11/60* (2006.01)

(52) U.S. Cl.
CPC .... *G06T 11/60* (2013.01); *G06T 2207/30004* (2013.01); *G06T 2207/30176* (2013.01); *G06T 2207/30196* (2013.01)

(58) Field of Classification Search
USPC ............................................................ 705/3
See application file for complete search history.

(56) References Cited

U.S. PATENT DOCUMENTS

| | | | |
|---|---|---|---|
| 8,385,616 B2 | 2/2013 | Futami et al. | |
| 9,177,110 B1 | 11/2015 | Fram | |
| 2002/0184053 A1 | 12/2002 | Arling | |
| 2003/0016850 A1* | 1/2003 | Kaufman | G06F 19/321 382/128 |
| 2003/0041112 A1* | 2/2003 | Tada | G06Q 10/107 709/206 |
| 2004/0078215 A1* | 4/2004 | Dahlin | G06F 19/322 705/2 |
| 2006/0139318 A1* | 6/2006 | Kariathungal | G06F 3/013 345/156 |
| 2006/0238546 A1 | 10/2006 | Handley | |
| 2007/0053567 A1 | 3/2007 | Adachi et al. | |
| 2007/0237378 A1 | 10/2007 | Reiner | |
| 2008/0091464 A1* | 4/2008 | Lipscher | G06Q 50/22 705/2 |
| 2008/0103828 A1 | 5/2008 | Squilla et al. | |
| 2008/0109250 A1 | 5/2008 | Walker | |
| 2008/0219523 A1 | 9/2008 | Brackett | |
| 2009/0192823 A1* | 7/2009 | Hawkins | G06F 19/321 705/3 |
| 2009/0198514 A1 | 8/2009 | Rhodes | |
| 2009/0248441 A1* | 10/2009 | Okada | G06F 19/321 705/2 |
| 2009/0262995 A1* | 10/2009 | Futami | G06F 19/321 382/128 |
| 2010/0053213 A1 | 3/2010 | Ishida et al. | |
| 2010/0100849 A1* | 4/2010 | Fram | G06F 3/0236 715/835 |
| 2010/0114597 A1 | 5/2010 | Shreiber | |
| 2010/0114610 A1* | 5/2010 | Schwalb | G06F 19/321 705/3 |
| 2010/0138239 A1* | 6/2010 | Reicher | G06F 17/243 705/3 |
| 2010/0268103 A1* | 10/2010 | McNamara | A61B 5/0402 600/518 |
| 2011/0087089 A1 | 4/2011 | Meinel et al. | |
| 2011/0153351 A1* | 6/2011 | Vesper | G06Q 10/10 705/2 |
| 2011/0161854 A1* | 6/2011 | Shukla | G06F 19/321 715/771 |
| 2011/0282687 A1 | 11/2011 | Koll | |
| 2012/0029943 A1* | 2/2012 | Kurahashi | A61B 6/563 705/3 |
| 2012/0054230 A1 | 3/2012 | Kanada | |
| 2012/0131436 A1* | 5/2012 | Leontiev | G06F 19/321 715/233 |
| 2012/0250961 A1 | 10/2012 | Iwasaki | |
| 2013/0110537 A1 | 5/2013 | Smith | |
| 2013/0132119 A1 | 5/2013 | Inmam | |
| 2013/0223708 A1 | 8/2013 | Fukatsu | |
| 2014/0149407 A1* | 5/2014 | Qian | G06F 19/321 707/737 |
| 2014/0172456 A1* | 6/2014 | Qian | G06F 19/3487 705/3 |
| 2014/0324477 A1* | 10/2014 | Oez | G06F 19/3487 705/3 |
| 2014/0344701 A1 | 11/2014 | Shreiber | |
| 2017/0039348 A1 | 2/2017 | Fram | |

OTHER PUBLICATIONS

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions, Accessed on Feb. 9, 2015.

Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BFB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf, Accessed on Feb. 9, 2015.

Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.

DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.

Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

Fujifilm Medical Systems, SYNAPSE® Product Data, Synapse Release Version 3.2.1, Server Modules and Interfaces, 4 pages color brochure, (XBUSSY085) Aug. 2008. Downloaded from http://www.fujifilmusa.com/shared/bin/server-interface.pdf. Accessed on Feb. 9, 2015.

(56) References Cited

OTHER PUBLICATIONS

Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com 13 Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/sceenshots.html. Accessed on Feb. 18, 2015.
ICRco, I See The Future, in 12 pages, color brochure, (BR080809AUS), © 2009 iCRco.ClarityPACS. Downloaded from http://www.claritypacs.com/pdfs/ISeeFuture_26_web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#Iproducts-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
LUMEDX CardioPACS 5.0 Web Viewer, Cardiopacs Module, 2 page color brochure, (5061-0011 Rev A). Downloaded from http://cdn.medicexchange.com/images/whitepaper/cardiopacs_web viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, a real-time picture archiving communication system, (PAX-21990 rev 2.0), 2 page color brochure. Downloaded from http://www.merge.com/MergeHeatlhcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scirmage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraradcorp.com/pdf/UltraVSION.pdf. Accessed on Feb. 9, 2015.
VioStream for VitreaView, 2 color pages printout. Accessed at http://www.vitalimages.com/solutions/universal-viewing/viostrearm-for-vitreaview. Accessed on Feb. 9, 2015.
Visage Imaging Visage 7, 3 color page printout. Accessed at http://www.visageimaging.com/visage-7. Accesed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
U.S. Appl. No. 14/966,934, Automated Report Generation, filed Dec. 11, 2015.
Handy (Screenshot of the commercial product Handy Patients Enterprise Edition that was publically available on the Internet at least on Jun. 2, 2010).

* cited by examiner

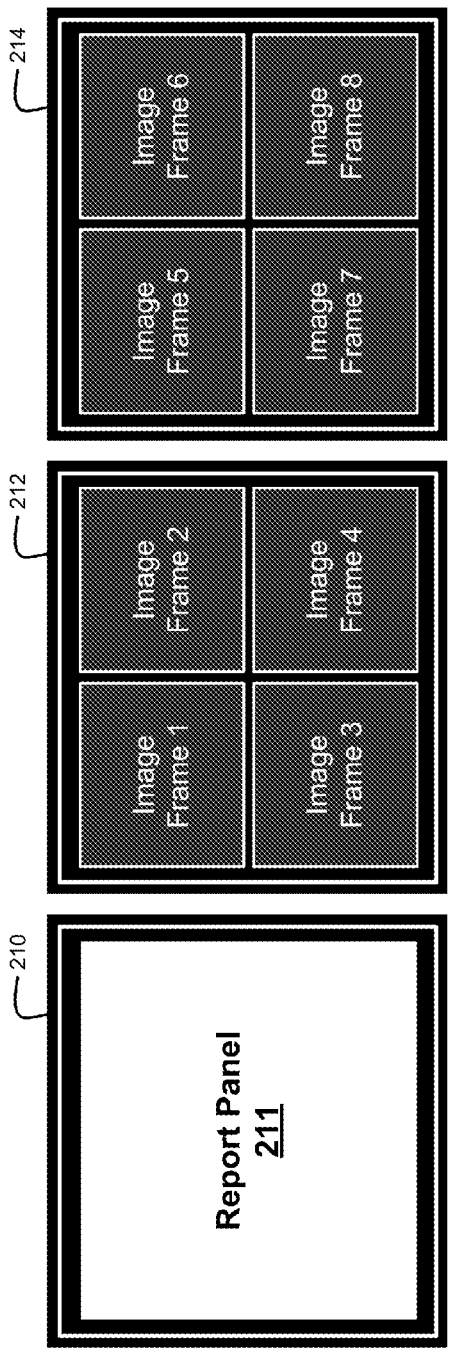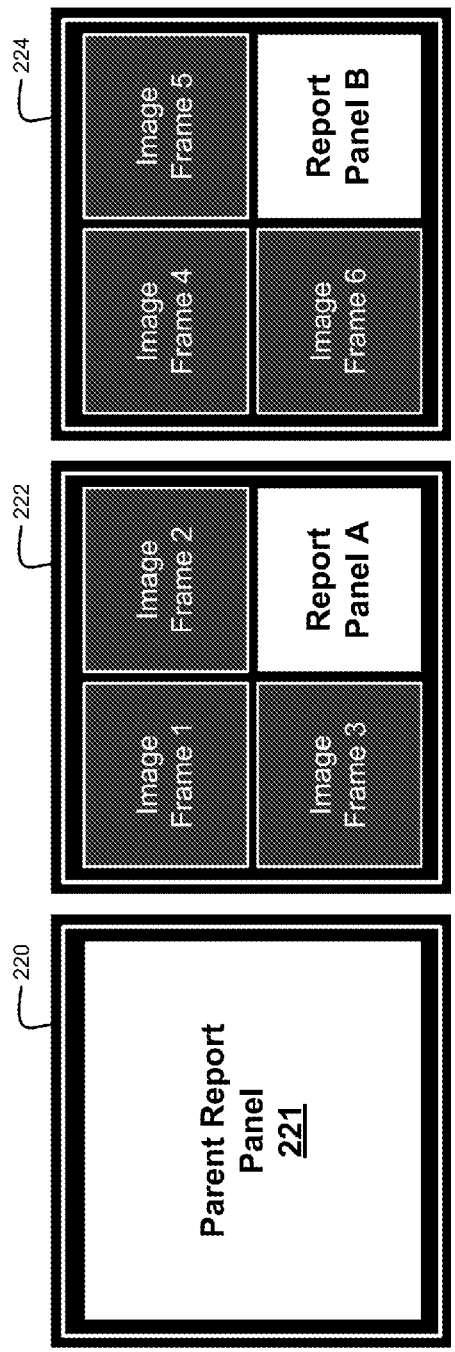

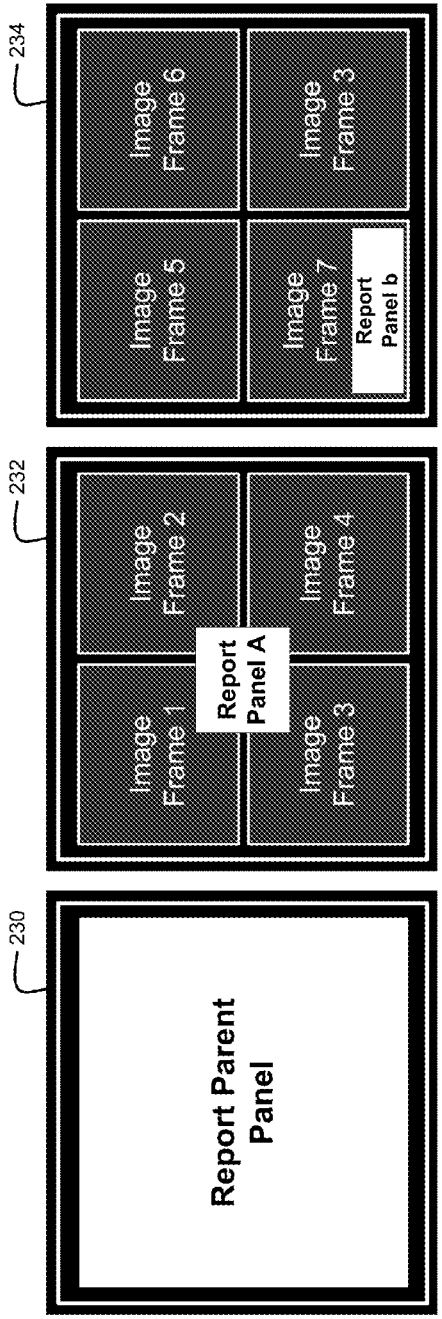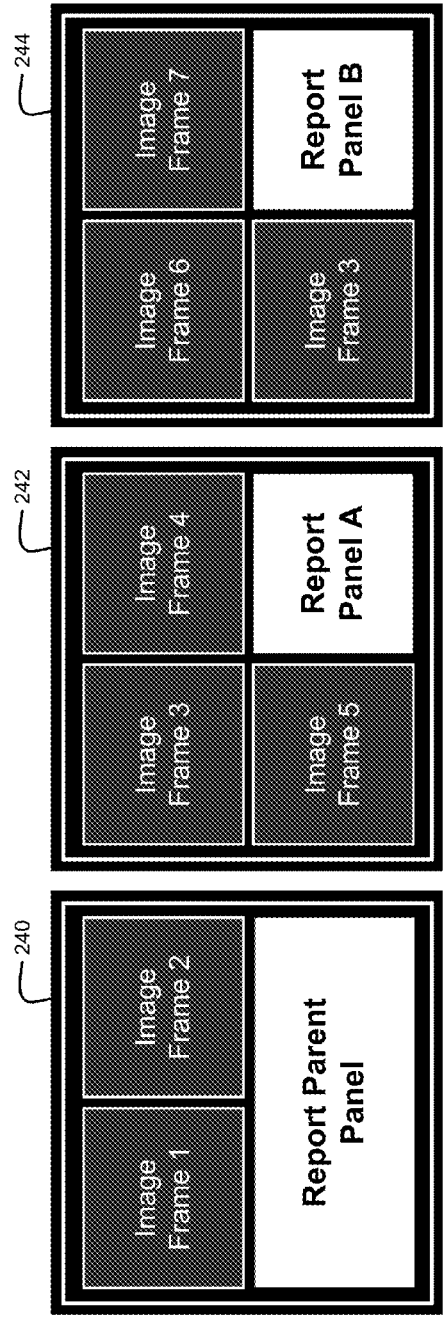
Fig. 2c
Fig. 2d

| 432 | L1-2 | L2-3 | L3-4 | L4-5 | L5-S1 |
|---|---|---|---|---|---|
| Central canal stenosis (grade) | normal | normal | mild | Moderate | severe |
| Left Neural Foramen (stenosis grade) | normal | normal | moderate | mild | severe |
| Right Neural foramen (stenosis grade) | normal | normal | normal | mild | moderate |
| Left Facet (hypertrophy grade) | normal | normal | normal | normal | severe |
| Right Facet (hypertrophy grade) | normal | normal | normal | normal | severe |
| Ligamentum Flavum (hypertrophy grade) | normal | normal | normal | normal | moderate |
| Extrusion | no | no | no | yes | no |
| Protrusion | no | no | no | no | no |
| size of Extrusion/Protrusion | - | - | - | small | - |
| location: Right neural foramen | - | - | - | - | - |
| location: Right paracentral | - | - | - | - | - |
| location: Central | - | - | - | yes | - |
| location: Left paracentral | - | - | - | - | - |
| location: Left neural foramen | - | - | - | - | - |
| Bulge | no | no | yes | yes | yes |
| Osteophyte | no | no | no | no | no |
| location (left, broad, right) | - | - | left | broad | broad |
| size (mild, moderate, large) | - | - | moderate | mild | large |

Fig. 4b

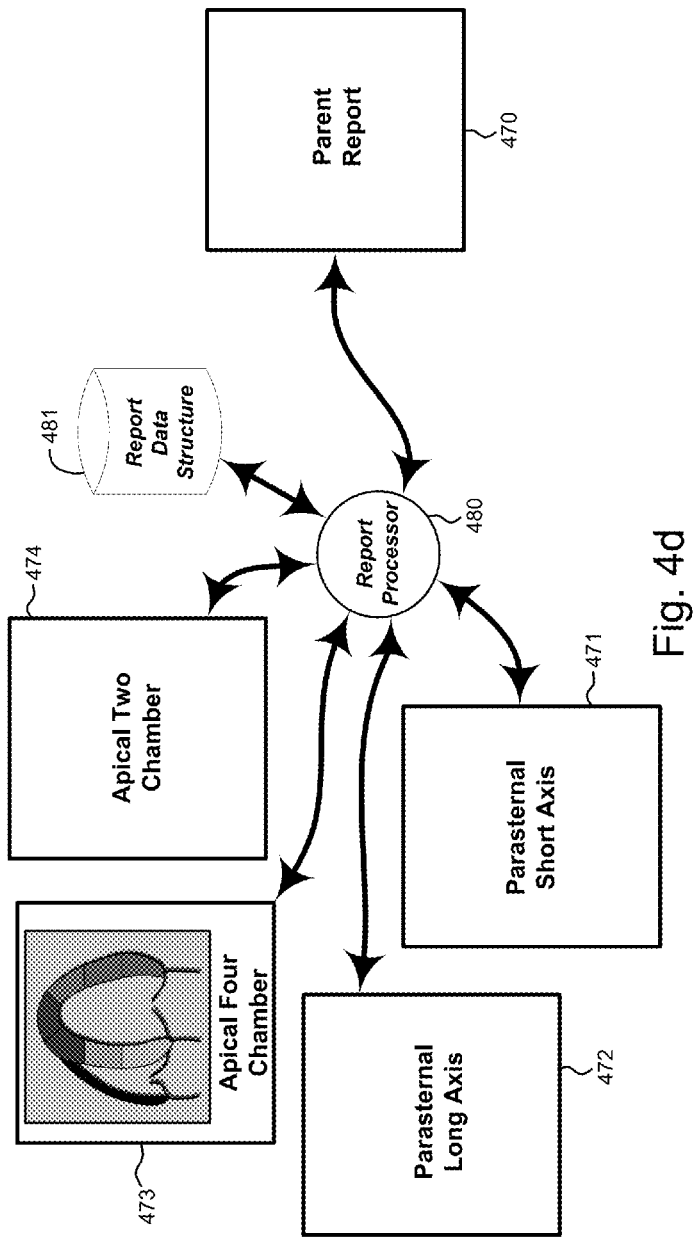

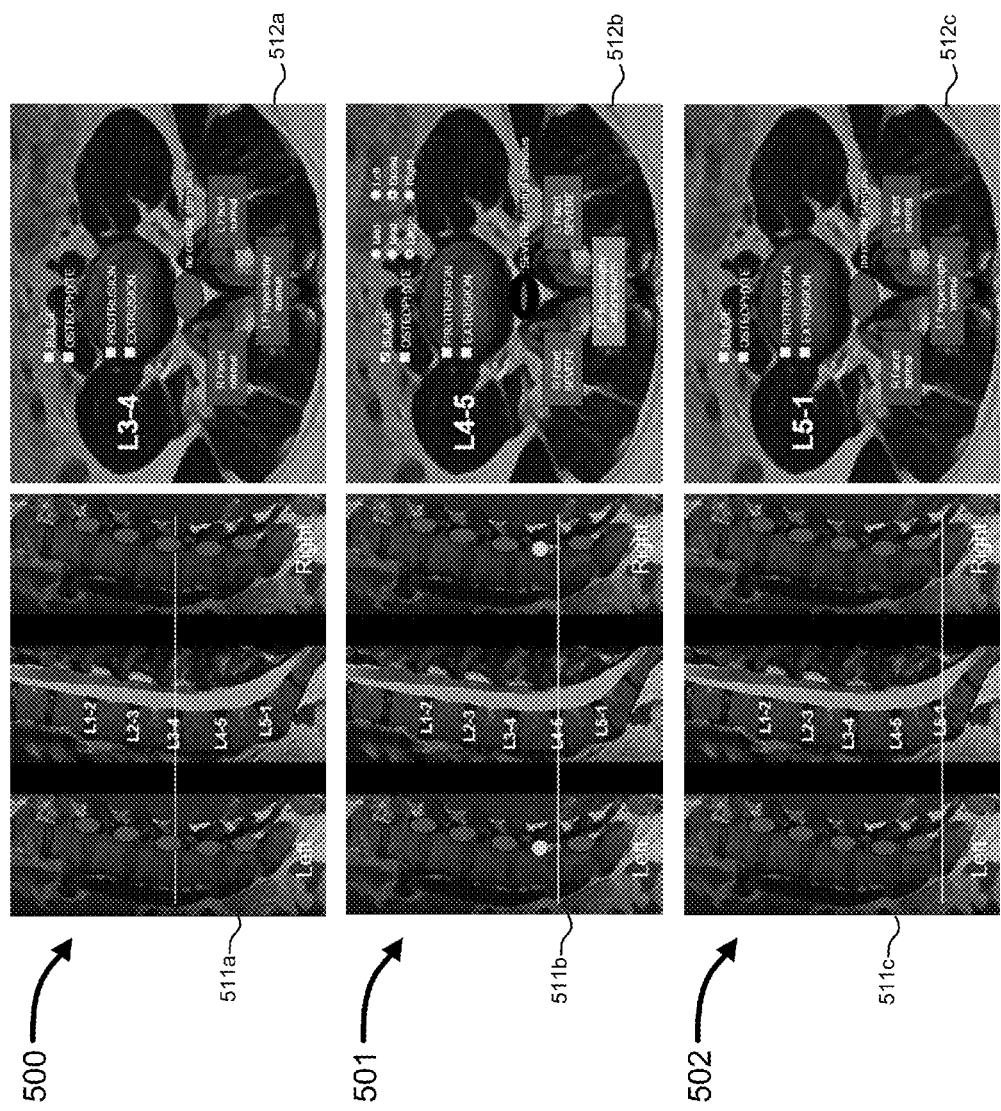

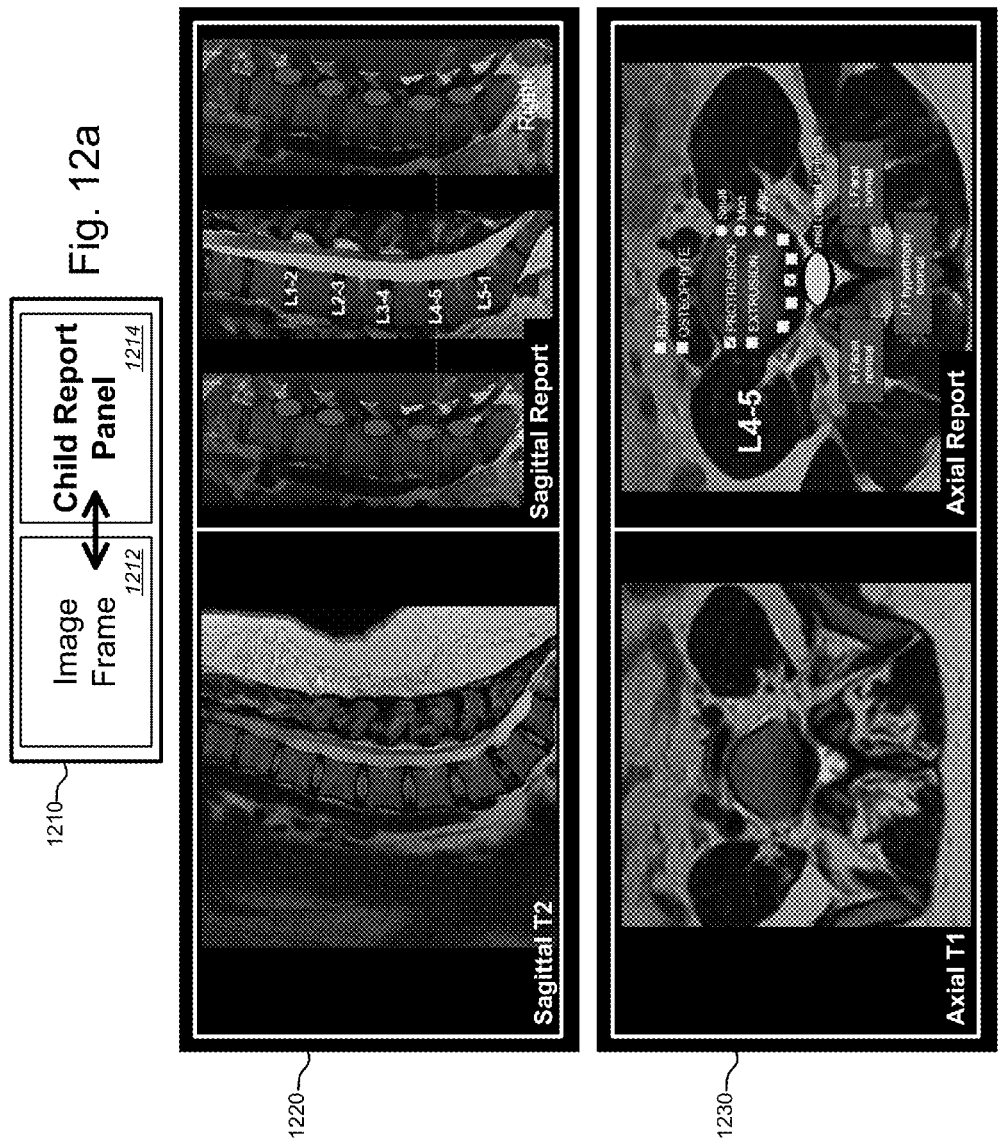

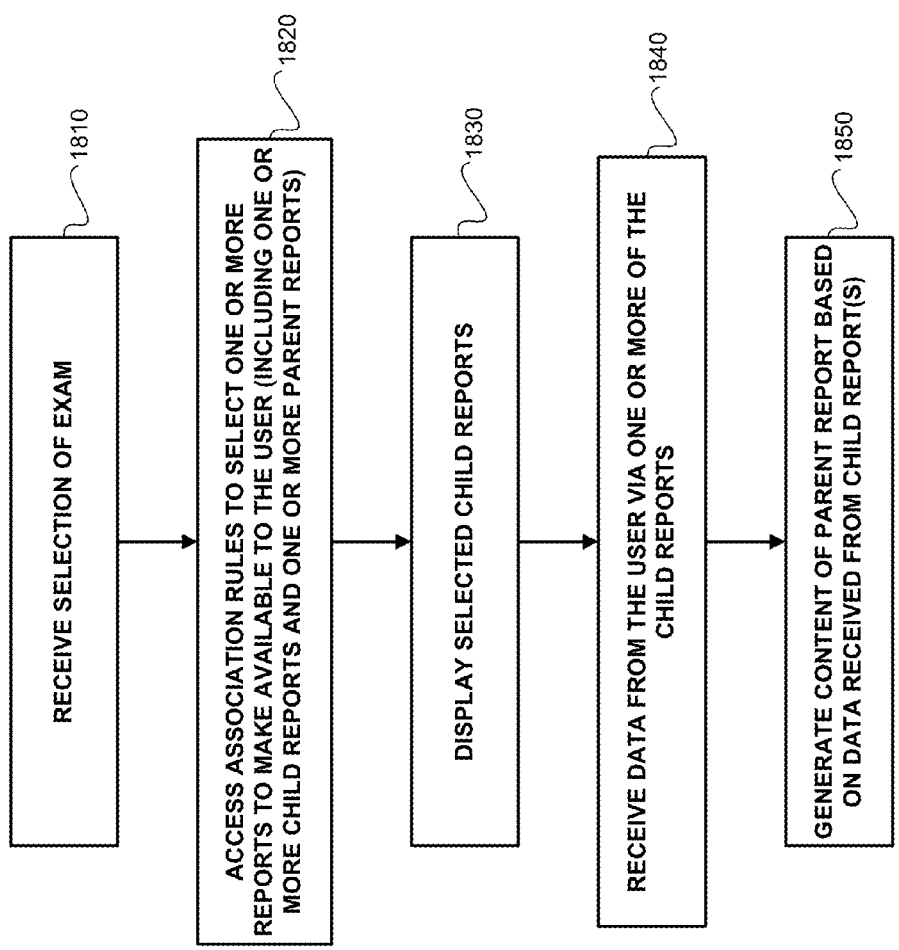

AUTOMATED REPORT GENERATION

CROSS-REFERENCE TO RELATED APPLICATIONS

This application is a continuation of U.S. patent application Ser. No. 13/530,754, filed Jun. 22, 2012, which application claims the benefit of priority under 35 U.S.C. §119(e) of U.S. Provisional Application No. 61/500,896, filed Jun. 24, 2011, the disclosures of which are hereby incorporated by reference in their entireties.

BACKGROUND

There is a need for innovations that increase the efficiency and accuracy of interpretation of medical imaging exams.

SUMMARY

In one embodiment, a method of generating a parent report comprising data associated with one or more child reports comprises receiving selection of an exam for display on a display device of a computing system having one or more computer processors and one or more displays, determining an exam characteristic associated with the exam, accessing a data structure storing associations between exam characteristics and respective report packages, each of the report packages comprising a parent report and one or more child reports, selecting from the data structure a report package associated with the determined exam characteristic, wherein the selected report package comprises a selected parent report and one or more selected child reports, and displaying one or more of the selected child reports on the one or more displays, wherein the selected child reports are configured to receive input from a user of the computing system that is usable in automatically generating content of the selected parent report.

In some embodiments, the selected report package further comprises a selected report processor including logic for accessing data provided in the selected child reports and updating the selected parent report. In some embodiments, the logic comprises software code, rules, and/or relationship data structures. In some embodiments, the selected report package further comprises a selected report data structure configured to store data received in the selected child reports. In some embodiments, the selected report processor is configured to initiate storage of data in the selected report data structure in response to user interactions with the selected child reports. In some embodiments, the exam comprises two or more image series and the data structure further comprises associations between image series types and child reports.

In some embodiments, the method further comprises determining a first series type associated with a first image selected for display by the user, and selecting a first one or more of the selected child reports for display based on an association between the determined first series type and the selected first one or more of the selected child reports in the data structure.

In some embodiments, the method further comprises, in response to the user selecting a second image for display, determining a second series type associated with the second image, selecting a second one or more of the selected child reports for display based on an association between the determined second series type and the selected second one or more of the selected child reports in the data structure, wherein the first one or more child reports includes at least one child report that is not included in the second one or more child reports.

In some embodiments, the first series type is determined based on DICOM header information associated with the first image. In some embodiments, the selection of the exam is performed automatically by the computing system in response to one or more user preferences, system preferences, site preferences, or software preferences.

In some embodiments, the selection of the exam is made by a user of the computing system.

In some embodiments, the parent report comprises a medical report for use by a referring doctor.

In some embodiments, one or more of the determined child reports are at least partially graphical so that the user can provide input in an intuitive manner.

In some embodiments, the selected report processor is configured to correlate user interactions with the at least partially graphical child reports to textual data for inclusion in the selected parent report.

In some embodiments, the method further comprises displaying the selected parent report on one or more of the displays. In some embodiments, the method further comprises updating content of the selected parent report in response to the user interacting with the selected one or more child reports without displaying the selected parent report on the one or more displays.

In some embodiments, the method further comprises displaying one or more image frames depicting respective images therein on the one or more displays concurrently with display of one or more of the selected child reports on the one or more displays.

In some embodiments, at least one of the selected child reports is superimposed on one or more of the image frames. In some embodiments, the at least one of the selected child reports superimposed on the one or more of the image frames is at least partially transparent.

In some embodiments, the data structure further comprises associations between characteristics of images of the medical exam and child reports. In some embodiments, the image characteristics comprise one or more of anatomy depicted, image number, or other DICOM attribute.

In some embodiments, the method further comprises determining a first image characteristic associated with a first image selected for display by the user, and selecting a first one or more of the selected child reports for display based on an association between the determined first image characteristic and the selected first one or more of the selected child reports in the data structure.

In some embodiments, the method further comprises, in response to receiving a request from the user to display one of the selected child reports not currently displayed on the one or more displays, updating one or more images displayed on the display based on associations between the requested one of the selected child reports and image characteristics of the one or more images in the data structure.

In some embodiments, the exam characteristic comprise one or more of an exam type, exam modality, clinical indication and/or other clinical information, medical history of a patient, or risk factors associated with the patient.

BRIEF DESCRIPTION OF THE DRAWINGS

FIG. 2a illustrates a three display configuration in which the left monitor is used to display a report panel and the remaining two monitors are used to display images in image frames 1-8.

FIGS. 2b, 2c, and 2d illustrate improved arrangements of image frames and report panels that are possible using various systems and methods discussed herein

FIG. 4b is an example of a report data structure.

FIG. 4d illustrates a report processor interacting with four child reports, a parent report, and a report data structure.

FIG. 4e is an example of a report data structure that could be used to store the user's assessment of 17 wall segments that are assessed from various image series, such as by providing input to one or more of the child reports illustrated in FIG. 4d.

FIG. 5a illustrates two report panels at three points in time in order to illustrate how changes in one report panel may result in changes in another linked report panel, for example through the use of a report processor as discussed with reference to FIG. 4a.

FIG. 12a illustrates an example image report hanging protocol that defines the layout of an image frame and child report panel, but in this embodiment does not define the image series to be displayed in the image frame.

FIG. 12b illustrates example displays of components based on the report hanging protocol of FIG. 12a.

FIG. 18 is a flowchart illustrating one embodiment of a method of generating a parent report (e.g., a textual report describing findings in a series of medical images) based on data received from a user via one or more child reports (e.g., graphical user interfaces with control that allow the viewer to intuitively provide findings regarding medical images).

DETAILED DESCRIPTION

Figure 1A:
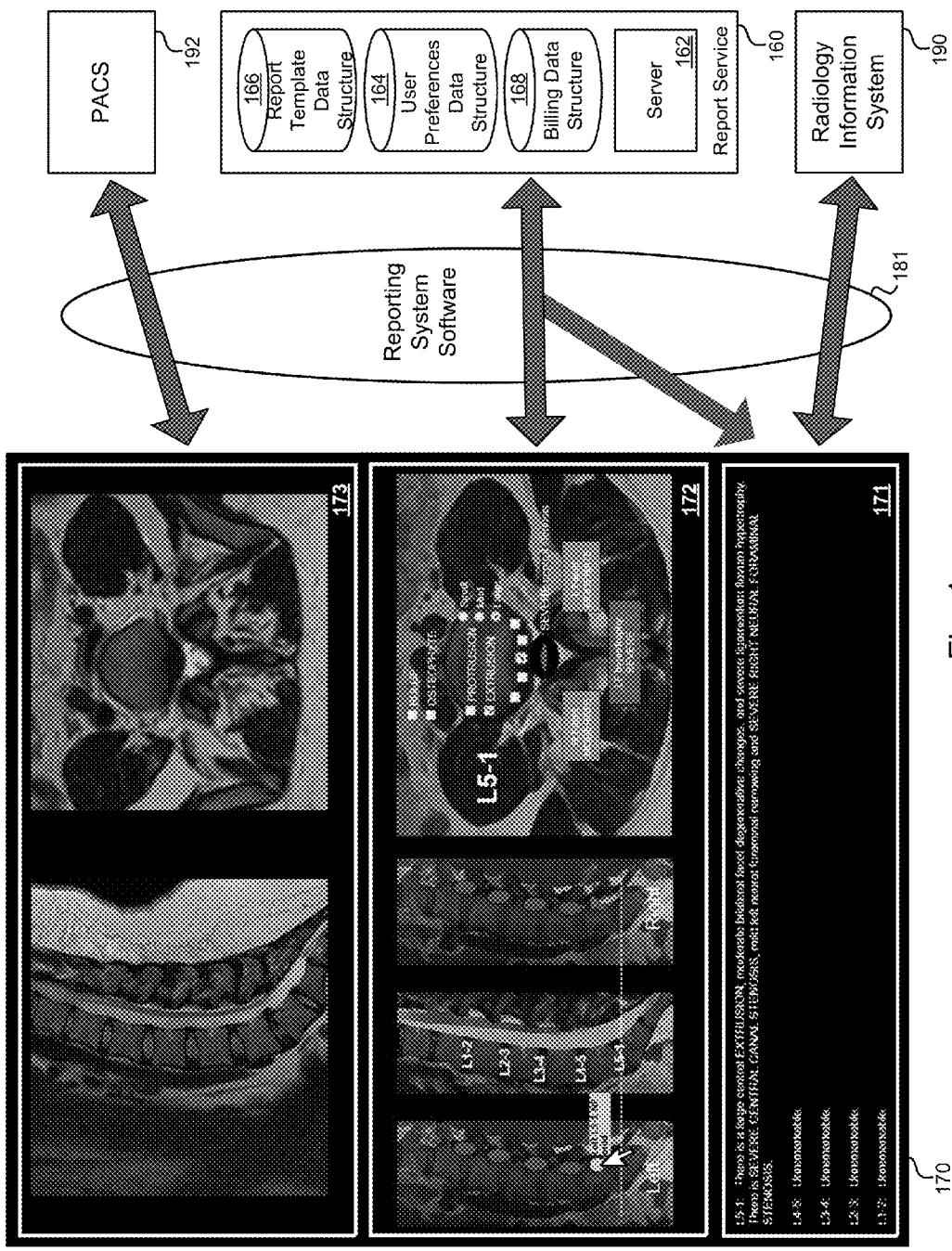
FIG. 1a is a block diagram illustrating a display of a computing device, wherein the computing device is in communication with various other components that are used by a user to view medical data and generate a report.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device. Users may include, for example, doctors, radiologists, hospital staff, or other individuals involved in acquisition, analysis, storage, management, or other tasks related to medical images. In other embodiments, users may include any individuals or groups of individuals that generate, transmit, view, and/or otherwise work with images of any type. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a tangible computer readable medium, such as a compact disc, digital video disc, flash drive, hard drive, memory device or any other tangible medium. Such software code may be stored, partially or fully, on a memory of a computing device (e.g., RAM, ROM, etc.), such as the computing device 150 (see discussion of FIG. 1, below), and/or other computing devices illustrated in the figures, in order to perform the respective methods. For ease of explanation, the methods will be described herein as performed by the computing device 150, but the methods are not limited to performance by the computing device 150 and should be interpreted to include performance by any one or more of the computing devices noted herein and/or any other suitable computing device.

Introduction

In many fields users view information and create reports documenting their observations and interpretations. For example, in the field of medical imaging, radiologists view medical imaging exams and create reports. In this example, medical imaging exams are typically viewed using a medical image management system, such as a Picture Archive and Communication System (PACS). The process of reporting typically involves the use of a Reporting System that may be a component of a Radiology Information System (RIS).

In practice, software used to display medical images, e.g. PACS, and the software used to create reports, e.g. digital dictation systems or radiology information systems (RIS), may be separate systems that are interfaced. Alternatively, the functionality of the systems may be on separate systems or integrated into a single system.

The software and user interfaces for viewing images, documents, etc., and generating a report may be responsive to various user interactions provided via a variety of input devices and/or methods, for example using a mouse, trackball, touch screen, keyboard, voice, and/or other methods. Reports may be displayed on a computing device so that the user can view and interact with the reports, for example by selecting items from drop down menus, provide input by keyboard, etc.

In practice, workstations used by radiologists to view exams and create reports often utilize multiple computer display devices, with a region of one monitor used to display a report and other monitors used to display images. For example, FIG. 2a illustrates a three display configuration in which the left monitor 210 is used to display a medical report panel 211 and the remaining two monitors 212 and 214 are used to display images. In practice, computer monitor 210 may be connected to a computer running reporting software (e.g., software configured to aid a radiologist in generating a medical report) and monitors 212 and 214 may be connected to a second computer running the PACS software. Alternatively, all three monitors may be connected to a single computer that is running both reporting software and PACS software, or some other combination of software that allows both viewing of medical images and report generation.

With the report physically separated from the images, such as in the embodiment of FIG. 2a, the user must move his attention and cursor from monitor to monitor. For example, when the user's attention is directed to Image Frame 6 of monitor 214, the user cannot easily observe the current status of the report panel 211 that the user is creating two monitors to his left on monitor 210. In practice, interaction with image frames (e.g., image frames 1-8 of FIG. 2a) and a report panel (e.g., report panel 211 of FIG. 2a) often requires the user to position a computer cursor over a region of interest. For example, if the user is interacting with image frame 6 (on monitor 214) and needs to then interact with the report panel 211 (on monitor 210), for example to choose a value from a drop down menu or change text, the user may need to reposition the cursor from the right monitor 214 to the left monitor 210 to interact with the report panel 211, and then back to the right monitor 214 to further interact with the images. This configuration may not optimize user efficiency and may contribute to repetitive motion injury and/or decreased reporting accuracy. Accordingly, there is a need for reporting methods that are more efficient, decrease cursor motion, and are potentially more accurate. Based on systems and methods described herein, reports may be divided into components that may be distributed across monitors, putting the relevant report component in close physical proximity to the relevant images within an exam. Examples based on systems and methods described herein are illustrated in FIGS. 2b, 2c, and 2d and will be discussed in more detail below.

Much reporting in medicine today involves text. Yet, conveying information may be more efficient using shapes and colors, for example, because interaction with graphics may be more intuitive and efficient than interacting with text. Based on systems and method described herein, efficient methods of leveraging both graphical and textual reporting are presented.

Medical imaging is a complex and evolving field. There is potential for a reporting system to improve the efficiency and accuracy of reporting by providing functionality and information relevant to clinical decision making. Based on systems and methods described herein, report templates tailored to various types of medical imaging exams and/or clinical indications could be created by subspecialty experts and made available to all users, regardless of the vendor of their reporting system, RIS, and/or PACS. This could be accomplished in a number of ways, including a cloud-based, vender-neutral, platform neutral service, as described in reference to FIG. 1a.

While systems and methods described herein will generally be illustrated as used in radiology, all systems and methods described herein may be applied to other fields of medicine, including radiology, cardiology, pathology, endoscopy, and dermatology, as well as to nonmedical fields.

Definitions

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Medical imaging exam: Medical imaging exams comprise data related to a medical procedure, such as medical images, medical reports, and/or related information. Medical imaging exams can be acquired by a number of different medical imaging techniques, including computed tomography (CT), magnetic resonance imaging (MRI), ultrasound, nuclear medicine, positron emission computed tomography (PET), digital angiography, mammography, computed radiography, digital radiography, fluoroscopy, images generated in medical pathology and endoscopy, and any other imaging techniques. Medical imaging exams may also include text reports, graphs, numerical information such as measurements, movies, sounds or voice data, and/or any other information that may be stored in digital format. Although much of the discussion herein is with reference to medical imaging exams, the systems and methods described may be used with other types of images and data. Thus, any reference to medical images may alternatively be construed to cover any other type of image.

Image Frame: A region of a computer display that may display an image.

Report Panel or Report Frame: A region of a computer display that displays information related to a report, such as a report template, a report that is being generated, updated, and/or modified by a user, and/or a final report.

Image Series or Series: Medical imaging exams are typically organized into one or more series, with each series including one or more images. Images in a series typically share one or more common characteristic, for example the type of anatomic plane and/or image orientation. Series may be characterized by their type. For example, series may be acquired using different pulse sequences, acquired in different anatomic planes, and acquired before or after administration of intravenous contrast material. In some embodiments a series may include other types of information, such as text reports, graphs, numerical information such as measurements, movies, sounds or voice data, and/or any other information that may be stored in digital format.

Example Configuration

FIG. 1a is a block diagram illustrating a display 170 of a computing device, wherein the computing device is in communication with various other components that are used by a user to view medical data and generate a report.

Example computer display 170 includes three regions: region 173 displays images from an example medical imaging exam, region 171 displays a parent report, and region 172 displays child reports related to the parent report, as will be described in more detail herein.

A report service 160, which may include one or more computing system, comprises one or more of the following:

A report template data structure 166 that contains one or more report templates, such as one or more parent report templates and/or child report templates.

A user preferences data structure 164 that associates report templates with medical imaging exams.

An optional billing data structure 168 that may be used in certain business models where reporting functionality is provided as a service.

An optional server 162 (e.g., a web server or other server) that may be used in certain configurations where the reporting functionality is provided via web-based or cloud-based technology. In other embodiments, communication between the various systems may occur using other types of technology and/or networks, such as those described with reference to FIG. 1b, for example.

In other embodiments, the report service 160 may include fewer or more components and/or components listed may reside in other systems. For example, in one embodiment the user preferences data structure 164 may be associated with a PACS system or a different system.

In the embodiment of FIG. 1a, a radiology information system (RIS) 190 may serve as a repository for reports. In other embodiments, another system may service this functionality, such as an EMR (electronic medical record system), HIS (hospital information system), PHR (personal health record system), PACS, etc.

In the embodiment of FIG. 1a, PACS 192 manages medical imaging exams and may provide the functionality to display medical images. In other embodiments, reporting system software described herein may provide that functionality. In other embodiments, other image management systems may be utilized, e.g. cardiovascular information system, digital pathology system, EMR, etc.

The reporting system software 181, described in more detail herein, manages the creation of reports, may communicate with a PACS, report service 160 and Radiology Information System 190 and/or other system such as an EMR. The reporting system software 181 may execute on the user computing device (e.g., the computing device that is couple to the display 170 and generates the regions 171, 172, and 173 for display to the user), on another computer device, such as a server that communicates with the user computing device as well as the various image and report management systems (e.g., PACS 192, RIS 190, and report service 160 in FIG. 1a), or on one of the existing devices involved in image and/or report management (e.g., the reporting system software 181 may execute on the PACS 192, RIS 190, and/or report service 160). The reporting system software 181 may include various components in different embodiments and may be executed on any combination of one or more computing devices, such as one or more of the computing devices discussed with reference to FIG. 1a or 1b.

Figure 1B:
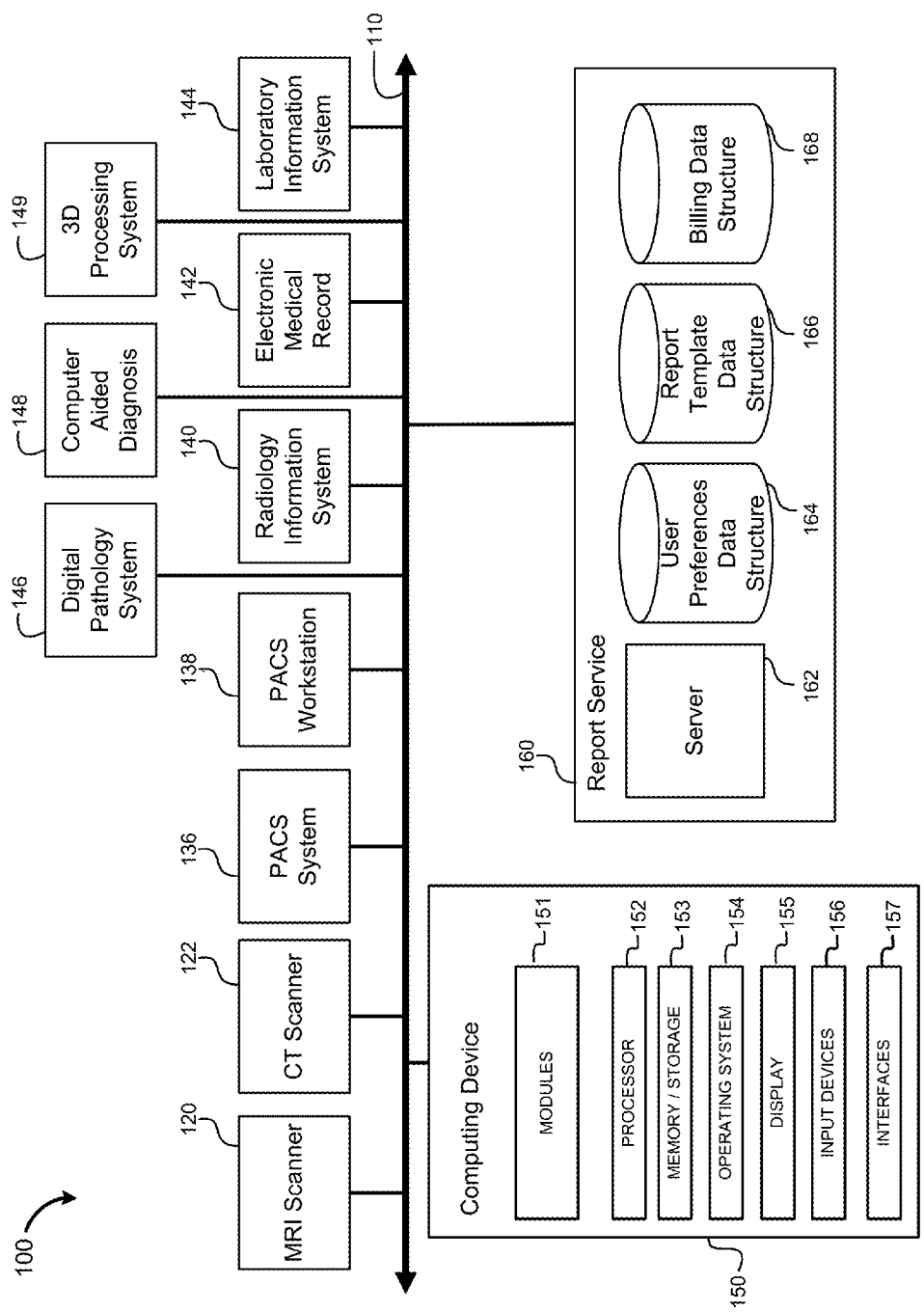
FIG. 1b is a system diagram which shows the various components of a system for managing data utilizing certain systems and methods described herein.

FIG. 1b is a system diagram which shows the various components of a system 100 for managing data utilizing certain systems and methods described herein. As shown, the system 100 may include a computing device 150 and may include other systems, including those shown in FIG. 1a.

The computing device 150 may take various forms. In one embodiment, the computing device 150 may be a computer workstation having modules 151, such as software modules. In other embodiments, modules 151 may reside on another computing device, such as a server (e.g., a web server or other server), and the user directly interacts with a second computing device that is connected to the web server via a computer network. In one embodiment, the modules 151 include some or all of the reporting system software 181 of FIG. 1a. The modules 151 will be described in detail below.

In one embodiment, the computing device 150 comprises a server, a desktop computer, a workstation, a laptop computer, a mobile computer, a Smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 150 runs an operating system 154, such as an off-the-shelf operating system, for example, Windows, Linux, MacOS, Android, or iOS operation system. The computing device 150 may also run a more specialized operating system which may be designed for the specific tasks performed by the computing device 150.

The computing device 150 may include one or more computing processors 152. The computer processors 152 may include central processing units (CPUs), and may further include dedicated processors such as graphics processor chips, or other specialized processors. The processors generally are used to execute computer instructions based on the software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, data structures, data structures, tables, arrays, and variables. For example, modules may include software code written in a programming language, such as, for example, Java, JavaScript, ActionScript, Visual Basic, HTML, Lua, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The computing device 150 may also include or be interfaced to one or more display devices 155 that provide information to the users. Display devices 155 may include a video display, such as one or more high-resolution computer monitors, or a display device integrated into or attached to a laptop computer, handheld computer, Smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The computing device 150 may also include one or more interfaces 157 which allow information exchange between computing device 150 and other computers and input/output devices using systems such as Ethernet, Wi-Fi, Bluetooth, as well as other wired and wireless data communications techniques. For example, the interfaces 157 may allow the computing device to communicate with various other devices via the computer network 110, which may take various forms. The computer network 110 may be a wired network or a wireless network, or it may be some combination of both. The computer network 110 may be a single computer network, or it may be a combination or collection of different networks and network protocols. For example, the computer network 110 may include one or more local area networks (LAN), wide area networks (WAN), personal area networks (PAN), cellular or data networks, and/or the Internet.

The modules of computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing device 150 may be combined into fewer components and modules or further separated into additional components and modules. Various other devices and subsystems may be connected to the network 110. For example, one or more medical scanners may be connected, such as MRI scanners 120. The MRI scanners 120 may be used to acquire MRI images from patients, and may share the acquired images with other devices on the network 110. One or more CT scanners 122 may also be coupled to the network 110. The CT scanners 122 may also be used to acquire images and, like the MRI scanner 120, may then store those images and/or share those images with other devices via the network 110. Any other scanner or device capable of inputting or generating information that can be presented to the user as images, graphics, text, or sound, including ultrasound, angiography, nuclear medicine, radiography, endoscopy, pathology, dermatology, etc.

Also connected to the network 110 may be a Picture Archiving and Communications System (PACS) 136 and/or PACS workstation 138. The PACS 136 is typically used for the storage, retrieval, distribution and presentation of images (such as those created and/or generated by the MRI scanner 120 and CT Scanner 122). The medical images may be stored in an independent format, an open source format, or some other proprietary format. A common format for image storage in the PACS system is the Digital Imaging and Communications in Medicine (DICOM) format. The stored images may be transmitted digitally via the PACS system, often reducing or eliminating the need for manually creating, filing, or transporting film jackets.

Also connected to the network 110 may be a Radiology Information System (RIS) 140. The radiology information system 140 is typically a computerized data storage system that is used by radiology departments to store, manipulate and distribute patient radiological information such as radiology reports.

Also attached to the network 110 may be an Electronic Medical Record (EMR) system 142. The EMR system 142 may be configured to store and make accessible to a plurality of medical practitioners computerized medical records. Also attached to the network 110 may be a Laboratory Information System 144. Laboratory Information System 144 is typically a system which stores information created or generated by clinical laboratories. Also attached to the network 110 may be a Digital Pathology System 146 used to digitally manage and store information related to medical pathology.

Also attached to the network 110 may be a Computer Aided Diagnosis System (CAD) 148 used to analyze images. In one embodiment, the CAD 148 functionality may reside in a computing device separate from the computing device 150 while in another embodiment the CAD 148 functionality may reside within the computing device 150.

Also attached to the network 110 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from computing device 150 while in another embodiment the 3D Processing functionality may reside within the computing device 150.

Also connected to the network 110 may be a Report Service 160 that may include one or more of the user preferences data structure 164, report template data structure 166, billing data structure 168, or server 162. In some embodiments, one or more of the data structures may be implemented as databases or may be implemented using a relational data structure, such as Sybase, Oracle, CodeBase and Microsoft® SQL Server as well as other types of data structures such as, for example, a flat file data structure, an entity-relationship data structure, an object-oriented data structure, and/or a record-based data structure.

In other embodiments, other computing devices that store, provide, acquire, and/or otherwise manipulate medical data may also be coupled to the network 110 and may be in communication with one or more of the devices illustrated in FIG. 1, such as with the computing device 150.

As will be discussed herein, computing device 150 may be configured to interface with various networked computing devices in order to communicate medical information that is stored among the various systems present in the network. In other embodiments, the computing device 150 may be used to display non-medical information.

Depending on the embodiment, the other devices illustrated in FIG. 1 (besides the computing device 150) may include some or all of the same components discussed above with reference to the computing device 150.

Example Layouts of Image and Report Frames

In practice, workstations used by radiologists to view exams and create reports often includes multiple monitors (and/or other computer display devices), with a region of one monitor used to display a report and other monitors used to display images. For example, FIG. 2a illustrates a three display configuration in which the left monitor 210 is used to display the report panel 211 and the remaining two monitors 212, 214 are used to display images in image frames 1-8. As noted above, however, this configuration may not optimize user efficiency and may contribute to repetitive motion injury and/or decreased reporting accuracy.

FIGS. 2b, 2c, and 2d illustrate improved arrangements of image frames and report panels that are possible using various systems and methods discussed herein. In the embodiments of FIGS. 2b, 2c, and 2d, relevant portions of the report are in close proximity to the images being interpreted, allowing more efficient correlation between images and the report, thus reducing cursor movement for navigation between images and reports. The example monitors of FIGS. 2b, 2c and 2d may be part of various embodiments of the computing device 150, or any other suitable computing system. For example, in the example of FIG. 2b, displays 220, 222, and 224 may be part of the display 155 of computing device 150 (FIG. 1b).

The layout of report panel(s) and image frames may be determined in various manners. For example, in some embodiments the screen layout of the report panels and image frames may occur automatically, for example by the computing device selecting content of a report panel in response to the specific content of one or more nearby image frames. In some embodiments, the screen layout of report panels and image frames may be based on hanging protocols and/or user preferences, for example based on exam characteristics such as scanner modality, exam type, and/or clinical indication. In some embodiments, the user may interactively change the layout, number, size, and/or content of report panels and image frames.

In the example of FIG. 2b, report panel A and report panel B, displayed on monitors 222 and 224 respectively, interact with a parent report panel 221 on monitor 220 based on systems and methods described herein. In some embodiments, report panels may be sized to be similar to image frames so they can be easily rearranged by the user in combination with image frames, for example. In some embodiments, report panels and image frames have different sizes.

Based on systems and methods described herein, the content of report panels A and B may be chosen automatically or manually to be relevant to the content of the image frames in close physical proximity. For example, the computing device 150 may automatically select content of report panel A based on one or more characteristics of images or series in image frames 1-3. Similarly, the computing device 150 may automatically select content of report panel B based on one or more characteristics of images or series in image frames 4-6.

In the example of FIG. 2c, report panel A and report panel B are floating panels that may be superimposed over one or more image frames. Based on systems and methods described herein, one or more of a report panel's characteristics, such as size, position, transparency, etc., may be automatically determined, modified by user input, and/or determined by user preferences. For example, a user may have a preference for report panels to be superimposed over a middle of multiple image frames, such as in display 232 or may have a preference for report panels to be superimposed in a particular screen locations, such as the lower left corner in the example of display 234. Additionally, the user may have preferences that automatically select a position for superimposing a report panel (or placing inline with image frames) based on various characteristics of the exam being view, the patent, a viewing environment, etc.

Depending on the embodiment, a parent report panel may or may not be present. As with the other report panels, characteristics of parent report panels may be changed manually by a user and/or automatically, such as based on user or system preferences. In the example of FIG. 2d, the parent report panel has been reduced in size compared to other examples, providing room on monitor 240 for the display of image frames.

Figure 3A:
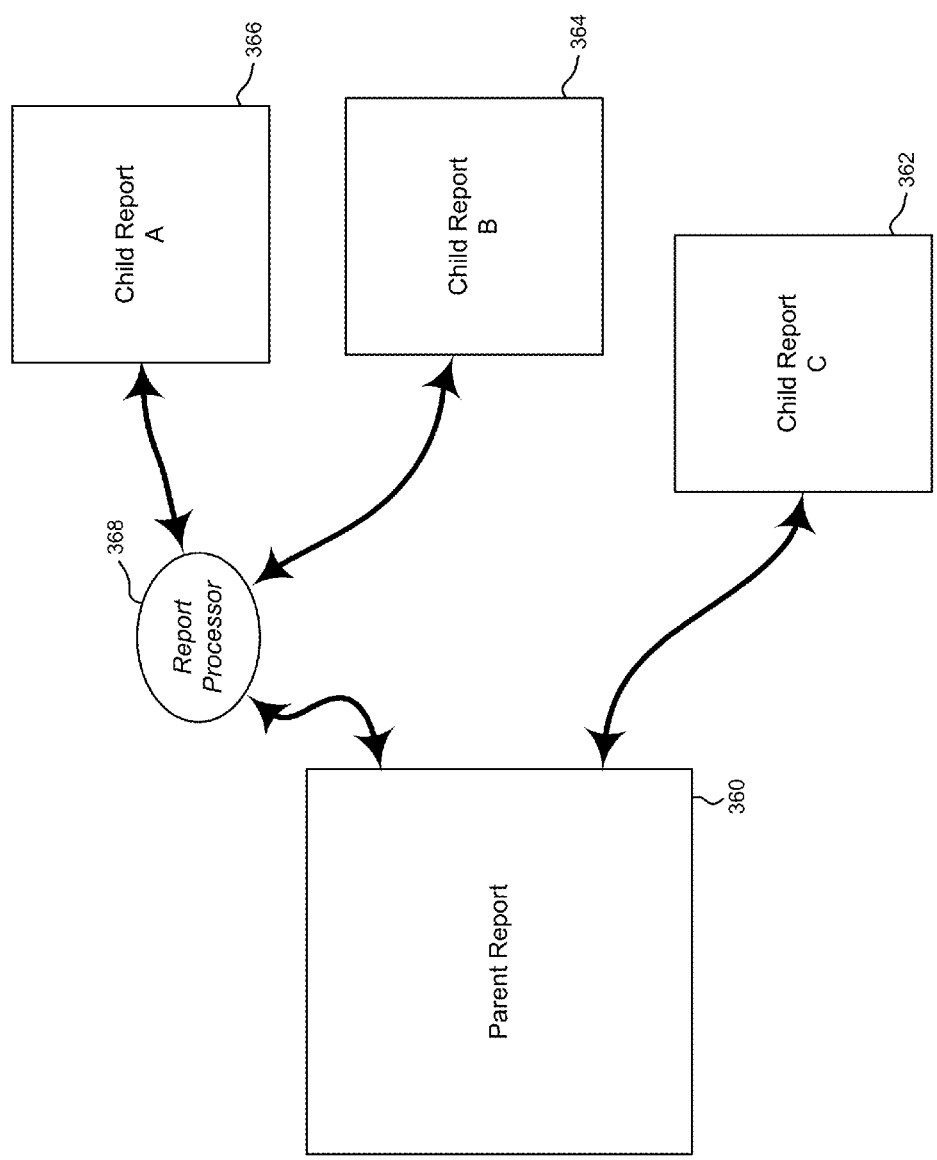
FIG. 3a is a block diagram illustrating interaction of multiple child reports with a parent report via a report processor.

FIG. 3a is a block diagram illustrating interaction of multiple child reports 362, 364, and 366 with a parent report 360 via a report processor 368.

Based on systems and methods described herein, a report package may include a parent report and one or more associated child reports. In one embodiment, report packages are associated with exam characteristics (e.g., exam types, clinical indications, clinical history, etc.), such that in response to selection of an exam by a user an appropriate report package comprising a parent report and one or more child reports may be selected. In some embodiments, report packages may include one or more report processors (discussed further below) configured to coordinate generation of parent report content based on user interactions with the one or more child reports of the particular report package. In some embodiments, report packages may include data structures for storing information regarding user interactions with the one or more child reports and/or content of the parent report.

One or more of a parent report and child reports may be displayed in report panels, for example as illustrated in FIGS. 2b, 2c, and 2d, with parent reports displayed in a parent report panel (e.g., the parent report panel illustrated on monitor 240 of FIG. 2d) and child reports displayed in report panels (e.g., the report panels A and B illustrated on monitors 242 and 244). Parent reports and child reports may contain a variety of types of information, such as textual information, numerical information, images, and/or graphical information.

In one embodiment, the number of child reports associated with a parent report (e.g., in a particular report package) may be based on predefined configurations, for example stored in Report Template Data structure 166 (FIG. 1a). In one embodiment, the number and content of child reports may change based on factors such as imaging modality, exam type, user preference, and/or user interaction.

One or more report processors 368 may include software that provides instructions, rules, software code, or other logic for processing of information within the child report(s) and parent report, and provides communication between these objects, as will be described herein. In one embodiment, the report processor 368 is software that is executed by the computing device 150 (FIG. 1b). In other embodiments, the report processor 368 comprises software executed by another computing device, such as a PACS, RIS, or other computing system.

For example, in one embodiment, report panels (e.g., depicting child reports) may contain graphics that can be manipulated by the user. These graphics may be processed to produce textual information by the report processor 368 that is included in a parent report, for example.

Figure 10:
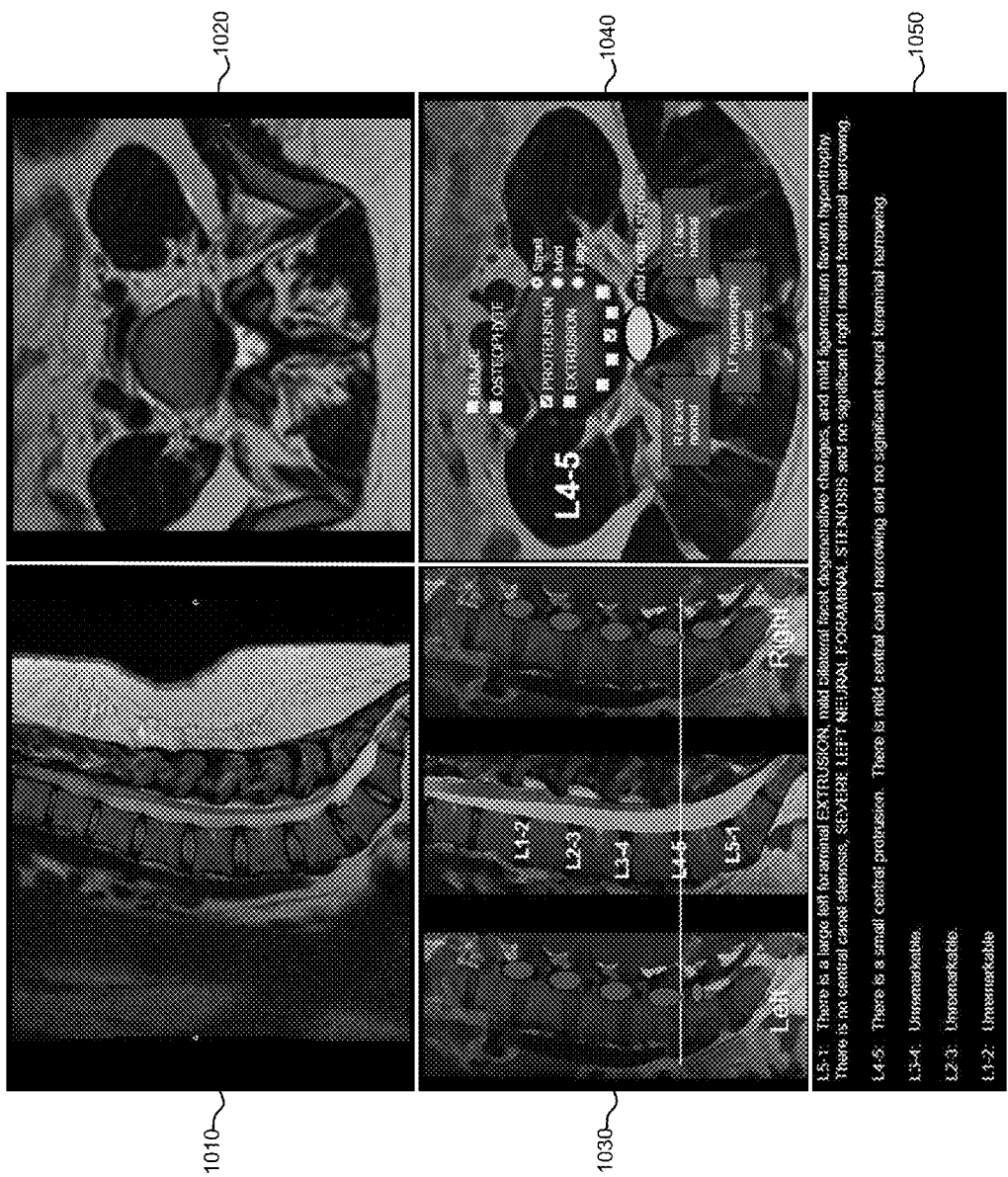
FIG. 10 illustrates image frames, report panels, and a parent report panel.

In the example of FIG. 10, which illustrates image frames 1010 and 1020, report panels 1030 and 1040, and parent report panel 1050 that are arranged according to a hanging protocol associated with the user, exam type, exam mortality, viewing environment, and/or any other attribute associated with the images, the user may interact with report panels 1030 and 1040 to graphically indicate abnormalities within the lumbar spine. This information is processed by a report processor that automatically creates a textual report describing the abnormalities, displayed in parent report panel 1050.

In some embodiments, changes made in a parent report may result in changes in one or more child reports through processing performed by a report processor.

Figure 3B:
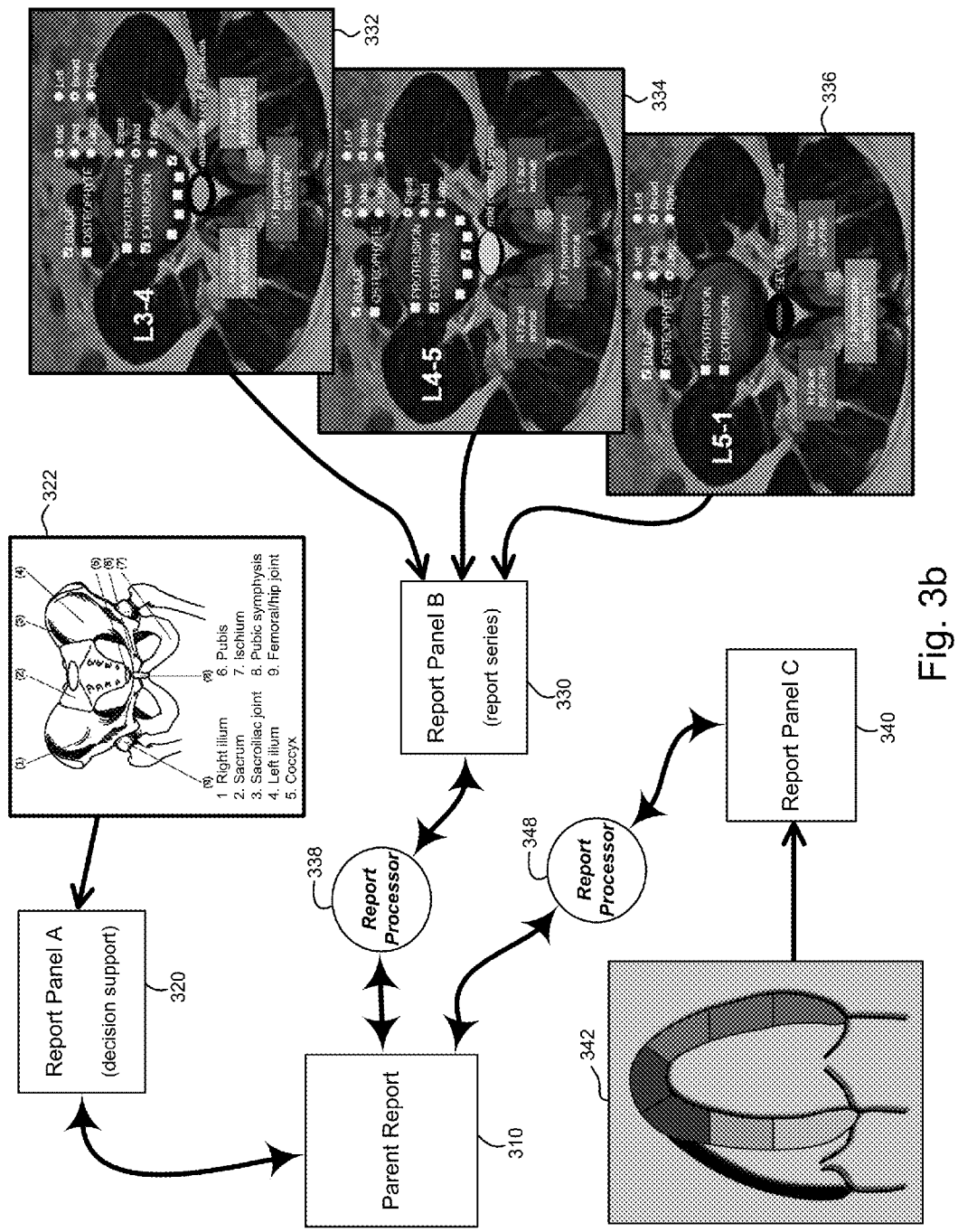
FIG. 3b is a block diagram illustrating certain interactions between a parent report panel and report panels including child reports, wherein the interactions are coordinated by a report processor or processors.

FIG. 3b is a block diagram illustrating certain interactions between parent report panel 310 and report panels 320, 330, and 340, that are coordinated by a report processor (or report processors). In one embodiment, the parent report 310 and three child reports 332, 334, and 336 are part of a report package that is associated with an exam type of the currently selected exam. For example, in response to the user selecting an exam for viewing, the computing device 150 may automatically select a report package associated with a determined type of the exam (and/or other characteristic of the exam), such that the combination of parent and child reports shown in FIG. 3b are automatically selected and available for display (and/or automatically displayed).

As noted above, child reports may be displayed in report panels on computer displays. The number, location, and or content of report panels may change during the course of use by a user, such as in response to changes in an image series of the exam that are selected for display and/or selection of different images (e.g., depicting different anatomies) for display. During the course of a user utilizing the system, the parent report and child reports may or may not be displayed in report panels.

In the example of report panel 320, the displayed content is a child report 322 that contains both text and graphics. In the example shown, child report 322 is a diagram of the human pelvis that includes anatomic labeling. Report panels can contain a variety of information, such as educational material, information that could aid in clinical decision making, etc.

In the example of report panel 330, one of a number of different child reports may be displayed, for example the illustrative child reports 332, 334, or 336, related to different levels of the lumbar spine. Report processor 338 may select various child reports for automatic display in a report panel based on a number of conditions. For example, the particular child report displayed in report panel 330 may change in response to user input or in response to changes in the content of another report panel or an image frame. For example, in one embodiment the child report displayed may change in response to content of an image frame linked to a report panel, such as is further illustrated in FIG. 5b.

In one embodiment, report processor 338 selects and/or creates textual information, for example in the form of sentences, phrases and or tables, based on graphical input that the user provides in report panel 330, and includes the textual information in the parent report, which may be displayed in a parent report panel to the user. In some embodiments, the report processor 338 may render graphical information in the parent report based on information in one or more child reports. In one embodiment, graphical information displayed in report panels and/or from child reports may be reproduced in the parent report and/or parent report panel.

In the example of report panel 340, child report 342 may be displayed. Manipulation of the content of report panel 340, such as interactions with the child report 342, allows the user to grade cardiac wall motion, for example. In the example shown, different cardiac wall motion grades are represented by different colors. Report processor 348 may communicate the wall motion grading for the various wall motion segments into the parent report 310, for example in the form of a table. In addition, a graphical representation of cardiac wall motion, for example similar to the example of child report 342, could be displayed in the parent report 310 and ultimately stored. This is discussed further with respect to other figures. In one embodiment, the report processor 338 and 348 are included in a single report processor, such as report processing software that is executed by the computing device 150.

Figure 4A:
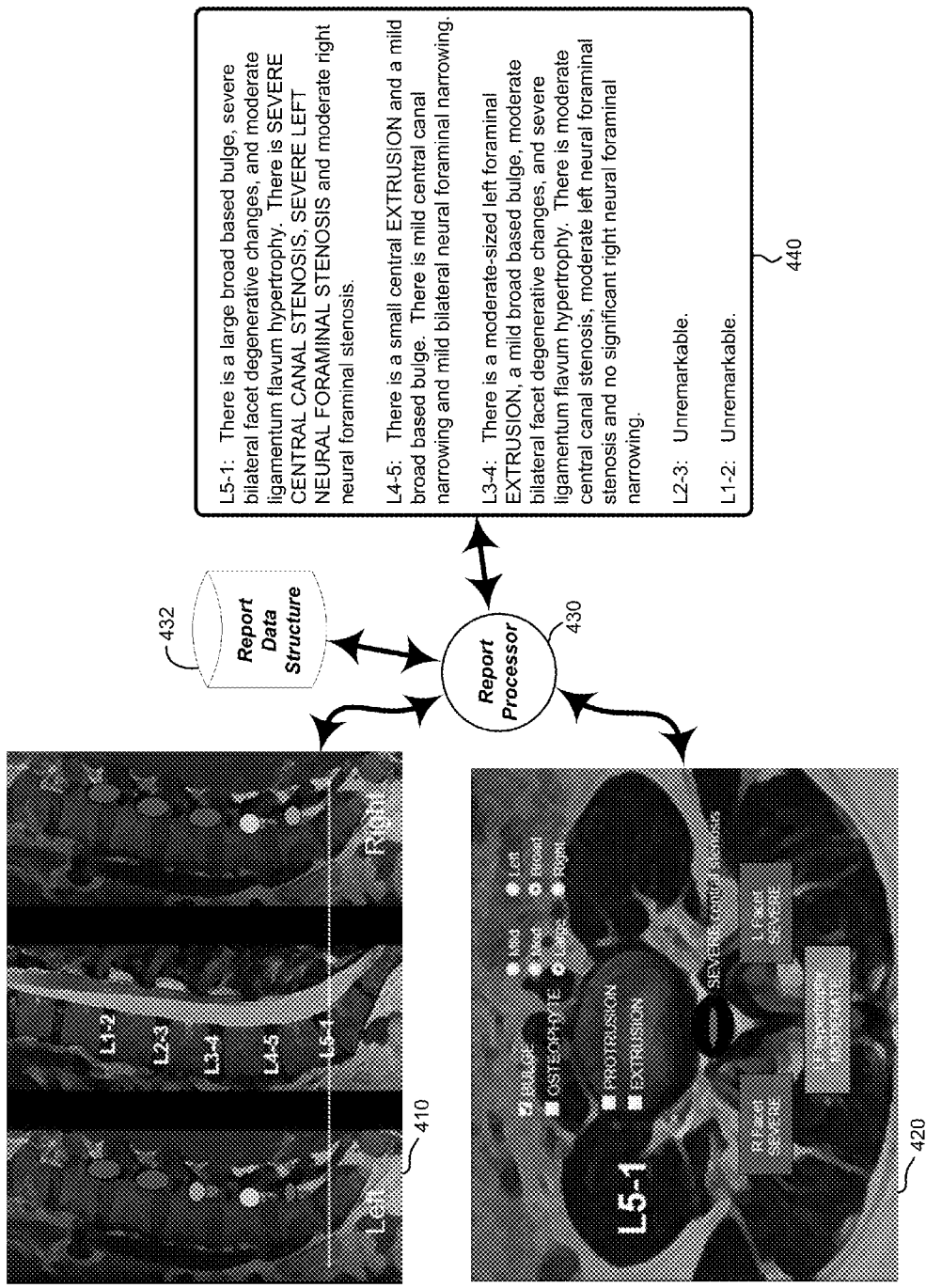
FIG. 4a is a block diagram illustrating example interactions of a report processor in generating a parent report.

FIG. 4a is a block diagram illustrating example interactions of a report processor 430 in generating a parent report 440. In this example, the report processor 430 interacts with two child reports 410 and 420, and a parent report 440.

In this example, the two child reports allow the user to input information related to a lumber spine MRI exam. For example, child report 410 depicts diagrams of sagittal views of a lumber spine MRI and allows the user to input information related to the neural foramina and child report 420 shows one of a series of graphics that represent axial levels of the lumbar spine (L1-2, L2-3, L3-4, L4-5 and L5-1), with L5-1 shown. Child report 420 allows the user to enter information related to the anatomic level being displayed by the report panel, in this example the L5-1 level. For example, the user can enter information related to central canal stenosis, the presence of extrusions, etc. Depending on the embodiment, the user can navigate through images that are displayed in the report panel, such as through the axial levels of the lumbar spine images in the example of FIG. 4a, in any suitable manner, such as via keyboard, touchpad, touchscreen, mouse, or other input. Movement between images may provide the user the ability to provide information regarding multiple images.

While the examples shown are related to a lumber spine MRI, in other embodiments the child reports may represent other types of information, for example related to Chest CT, Cardiac Ultrasound, Brain MRI, Chest Radiograph, PET, etc.

In order to produce parent report 440, information from the child reports 410 and 420 (e.g., in report panels on a display) is processed by report processor 430. In the example illustrated, information entered graphically in child reports 410 and 420 is processed to produce textual information included in the parent report 440.

In one embodiment, certain types of information are automatically presented differently in the text, for example to highlight their importance. For example, important findings might be presented in capital letters, a bold font, or different color. In the example of parent report 440, findings that are severe are automatically presented in capital letters as are the clinically significant findings of an extrusion. Depending on the embodiment, the report processor 430 may automatically identify important findings and modify text associated with those findings. For example, report processor 430 may access a database of terms associated with important findings (e.g., severe, remarkable, extrusion, etc.) in order to identify text to highlight in the parent report 440.

In some embodiments report processors communicate with one or more report data structures that store information related to child reports and/or parent reports. In the example illustrated, report processor 430 communicates with report data structure 432 that holds data related to information that the user has entered via interaction with child reports, even for those that may not be displayed in report panels. For example, a report data structure may store the degree of central canal stenosis for each lumber level, including for child reports that may not be currently displayed. The report data structure 432 may be used in conjunction with the report processor 430 that generates the text in the parent report 440 shown. An example report data structure is illustrated in FIG. 4b.

Interaction with one child report may change information in another child report based on the functionality of the report processor. For example, the user may change the lumber level in either child report and it is automatically reflected in both child reports. The communication of information from one report panel to another may occur via the report processor 430, which may be executed by any suitable computing device, such as computing device 150 of FIG. 1b.

In some embodiments, the textual data of a parent report, such as parent report 440, is updated in realtime as data in one or more child reports is provided and/or changed. Thus, the user can monitor how the textual report is updated in response to his input into the child reports.

FIG. 4b is an example of a report data structure, such as report data structure 432 in FIG. 4a. In this the example, content of the data structure relates to structures within a lumbar spine and the report data structure shown could be used in conjunction with the example illustrated in FIG. 4a. In this example, the report data structure 432 stores data received via one or more child reports and/or parent reports. For example, data related to bulge and osteophyte (e.g., the last four rows of report data structure 432) may have been provided via user interactions with a first child report, while data related to protrusions (e.g., the seven rows above the bulge row) may have been provided via user interactions with a second child report. In other embodiments, other report data structures may be used for storage of user-received data from one or more child reports.

Figure 4C:
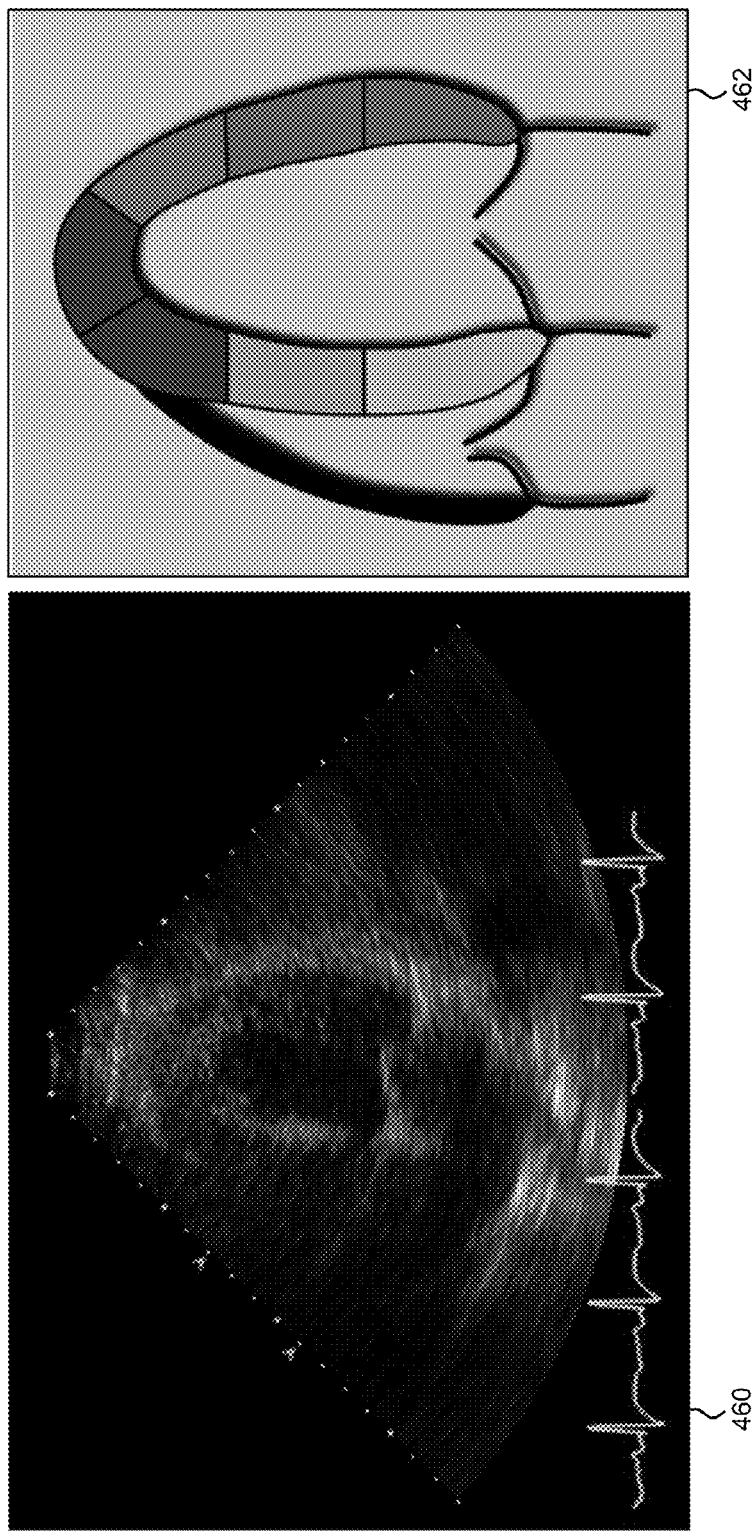
FIG. 4c illustrates an image frame that displays an image from an image series, in this example a series of images from a cardiac ultrasound acquired in an apical four chamber view and a report panel that displays a child report that a user can use to grade seven wall segments of the heart visible in images acquired in the apical four chamber view.

FIG. 4c illustrates an image frame 460 that displays an image from an image series, in this example a series of images from a cardiac ultrasound acquired in an apical four chamber view and report panel 462 that displays a child report that a user can use to grade seven wall segments of the heart visible in images acquired in the apical four chamber view. In practice, this image series and child report may be displayed on a computer monitor to allow the user to view a cine loop of the ultrasound images acquired in the apical four chamber view and efficiently grade the cardiac wall motion by interacting with the child report in the report panel 462.

There are portions of the heart wall that are not visible in the apical four chamber view so other views may also be examined by the user. For example, in cardiac ultrasound, four standard views may be obtained and examined to grade, for example, 17 wall segments.

FIG. 4d illustrates a report processor 480 interacting with four child reports 471, 472, 473, and 474, parent report 470, and report data structure 481. In this example, the four child reports correspond to four different cardiac ultrasound views. By interacting with each of these four child reports, the user may grade all 17 cardiac wall segments. Some wall segments may be visible in more than one view and therefore may be graded in more than one child report. In one embodiment, changing a wall segment grade in one child report automatically updates the grade displayed in the other child reports. In one embodiment, if data for a particular item (e.g., a grade for a wall segment) received in a child report differs from data for the same item received in a different child report, the user is given options to reconcile the different data. For example, the user may be able to select data provided in one of the child reports for use in both child reports, provide other data for use in one or both of the child reports, indicate that an average or compilation of data received in each child report are included in both child reports and/or the parent report, or any number of other reconciliation options. In one embodiment, the user may have a default preference for reconciliation, such that non-matching data is automatically updated according to the user preference.

FIG. 4e is an example of the report data structure 481 that could be used to store the user's assessment of 17 wall segments that he assesses from various image series, such as by providing input to one or more of the child reports 471, 472, 473, and 474. The report processor 480 (FIG. 4d) interacts with the four child reports shown, storing information entered by the user in report data structure 481, and transferring information to parent report 470.

FIG. 5a illustrates two report panels 511 and 512 at three points in time in order to illustrate how changes in one report panel may result in changes in another linked report panel, for example through the use of a report processor as discussed with reference to FIG. 4a.

View 500 shows report panels, 511a and 512a, which are example child reports relate to assessment of lumbar spine MRI exams. Report panel 511a depicts sagittal diagrams of a lumbar spine MRI and demonstrates a horizontal white line at the L3-4 level, indicating the active level for reporting. Report panel 512a depicts a child report showing a diagram of an axial view of the lumbar spine at the same L3-4 level, as depicted by the "L3-4" label on the child report.

Through systems and methods described herein, manipulation of one report panel may result in changes in another report panel. For example, the user may interact with report panel 511a by clicking the mouse cursor over a disk space label, e.g., "L4-5". This could cause the white marker line to be positioned at that level, changing the active level for reporting, as shown in report panel 511b of view 501, which depicts the same report panels 511 and 512 as in view 500, but after the user has selected a new disk space level. The linked report panel 512b would then display a child report that is relevant to the newly chosen level, here "L4-5". As another example, the user could position the cursor over the spine canal in the midline sagittal diagram depicted in report panel 511a, the region just to the right of the disc labels, and roll the a mouse cursor up or down to position the level of interest to another disc level.

Just as changes in the left report panel 511a may result in changes in the right report panel 512a, changes in the right report panel 512a may result in change in the left report panel 511a. For example, the user might position the cursor over the region of the "L3-4" disc space label in report panel 512a and roll the a mouse cursor up or down to position the level of interest to other disc levels and to cause report panel 511a to be updated to match the currently selected level.

In the embodiment of FIG. 5a, any change in disc space level made in one of the report panels 511 or 512 would be reflected in both report panels 511 and 512.

In view 501, the user has chosen the L4-5 level, for example using the interactions described above or other interactions involving a keyboard, touchscreen, mouse, trackball, voice control or other input device. Note that the left report panel 511b highlights the L4-5 level via the horizontal white line. In addition, the right report panel 512b is updated to show information related to the L4-5 level, including information related to bulges, osteophytes, right and left facet hypertrophy, central canal stenosis, etc. The user can manipulate this information.

In view 502, the user has chosen the L5-1 level and the report panels 511c and 512c reflect that choice, as discussed with reference to view 501.

Figure 5B:
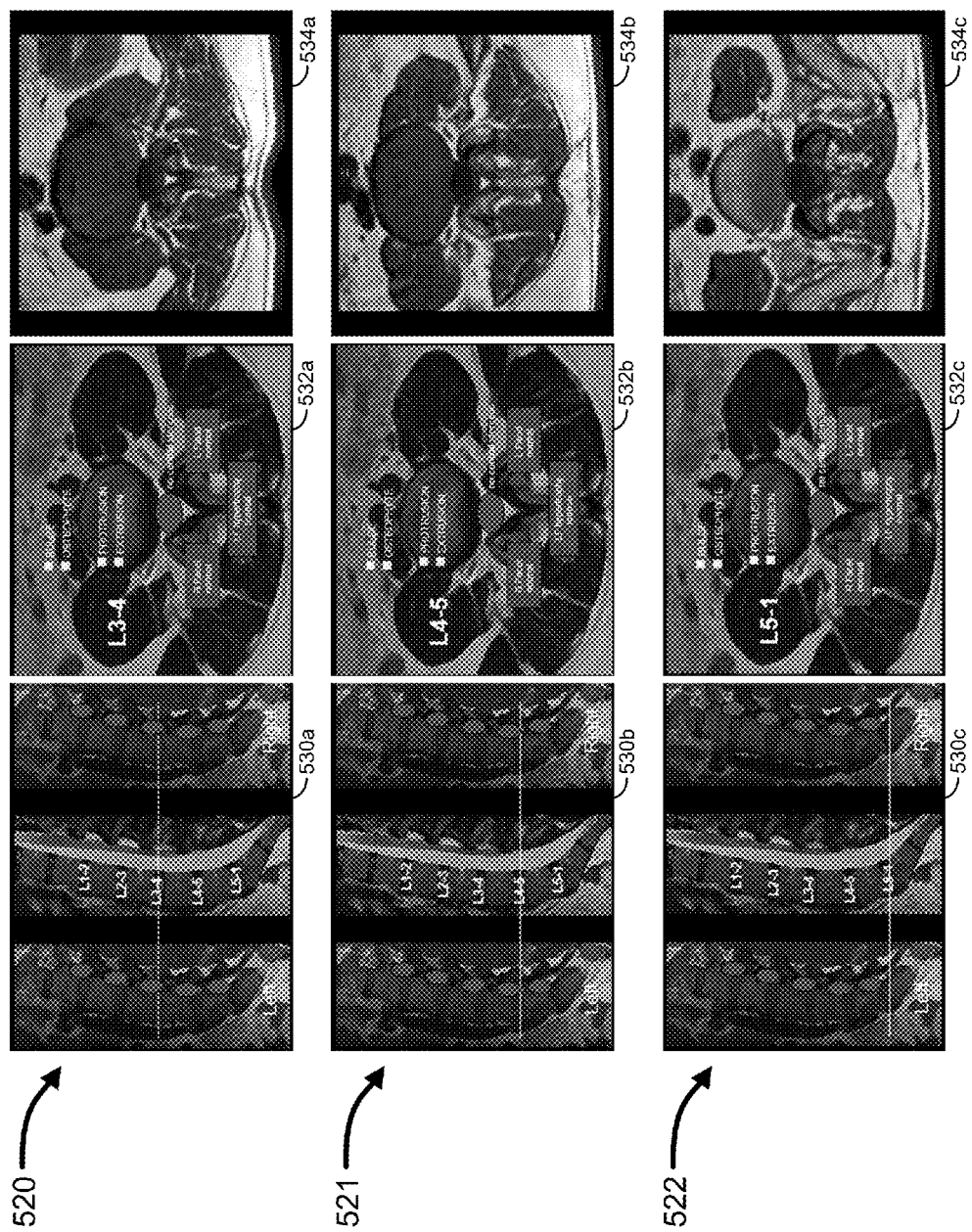
FIG. 5b illustrates one image frame and two report panels at three different points in time, wherein the image frame and report panels are linked, such that changes to one component may affect the display of the other components.

FIG. 5b illustrates one image frame 534 and two report panels 530 and 532 at three different points in time, wherein the image frame 534 and report panels 530 and 532 are linked, such that changes to one component may affect the display of the other components. For example, changes in the report panel 530 or 532 may result in changes in the image frame 534. In another embodiment, changes in the image frame 534 may result in changes in one or more of the report panels 530 or 532. In another embodiment, changes in either result in changes in the other.

Three views are illustrated, views 520, 521, and 522, showing different contents of report panels 530, 532 and one image frame 534, at different times that are indicated by the a, b, and c following the reference numbers 530, 532, 534. In other embodiments, different numbers and positions of report panels and image frames may be utilized.

In view 520, report panels 530a and 532a depict the L3-4 level, and image frame 534a depicts an axial image at the L3-4 level from an axial T1 series of a lumber spine MRI.

View 521 illustrates the scenario where the user has interacted with the image frame 534a to select a different level, level L4-5 in this example. Thus, the image now displayed in image frame 534b is an image at the L4-5 level. So that the system is efficient to use, the system automatically changes the contents of the report frames 530b and 532b so that they are now "positioned" at the L4-5 level. Accordingly, in this embodiment associations between child reports and images are defined and used in order to automatically select and display the appropriate child report in view of a currently displayed image, as the user selects various images in the exam. In one embodiment, different child reports may be selected in response to selection of particular images for display (e.g. child report 530a associated with level L3-4 may be a different child report than is shown in report frame 530b associated with level L4-5). In other embodiments, child reports are dynamically updated to display updated information in response to selection of particular images for display (e.g., the child report in report frame 530b may be the same child report as shown in report frame 530a, but with the currently selected level updated).

Similarly, view 522 illustrates the scenario where the user has interacted with the image frame 534b to select a different level, level L5-1 in this example. In response to selection of a new level in the image frame 534b, the report processor automatically selects child reports displayed in report panels 530c and 532c, which display information related to the newly selected level. Thus, as noted above, in this embodiment there is a linkage between the image frame and report frames such that a change in the content of the image frame changes the content of the report frames.

In another embodiment, changes in the report frame result in changes in one or more image frames. For example, the user could manipulate the level of interest in either report frame, for example as discussed with reference to FIG. 5a, and the anatomic level displayed in the image frame would be automatically changed to reflect the anatomic level chosen in the report frame.

Figure 14:
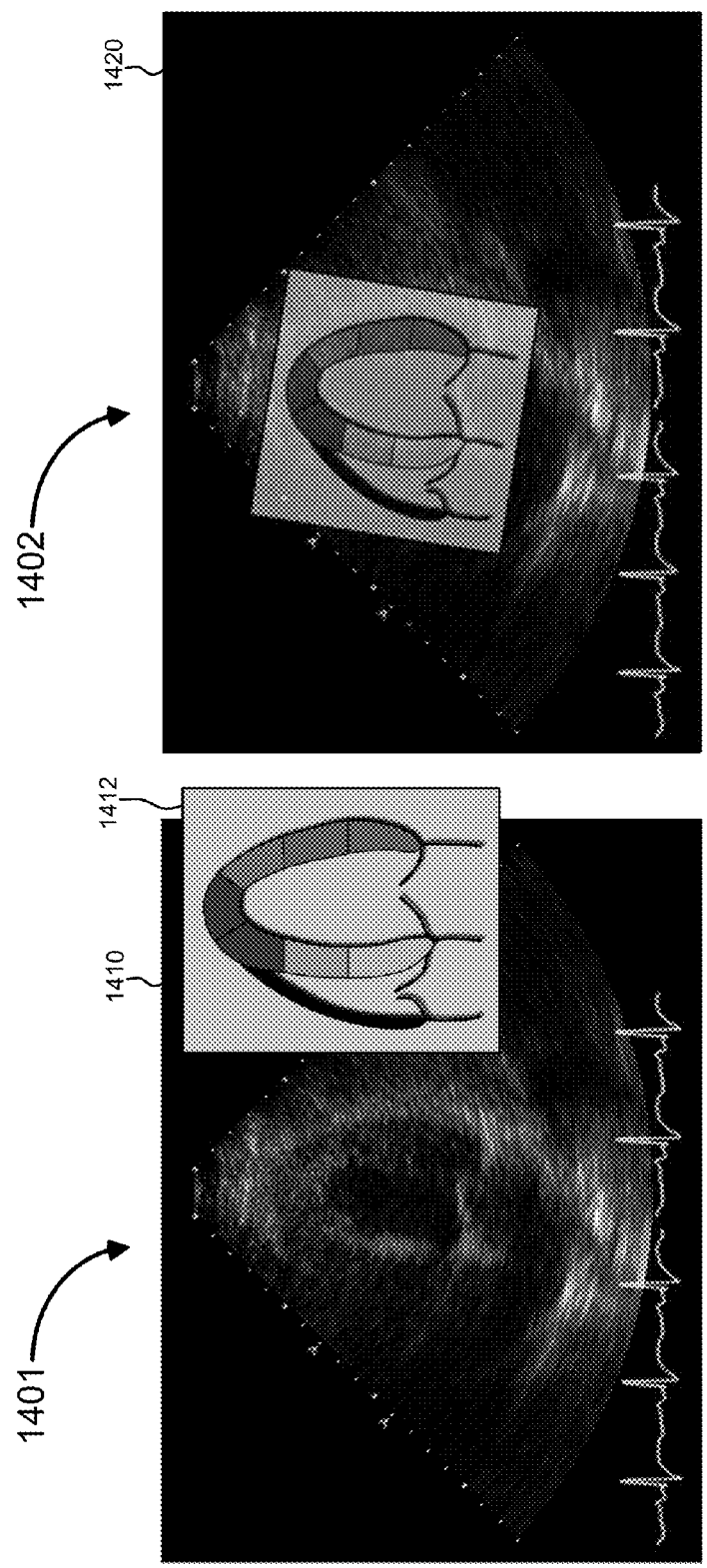
FIG. 14 illustrates image frames with a report panel superimposed in different manners.
Figure 15:
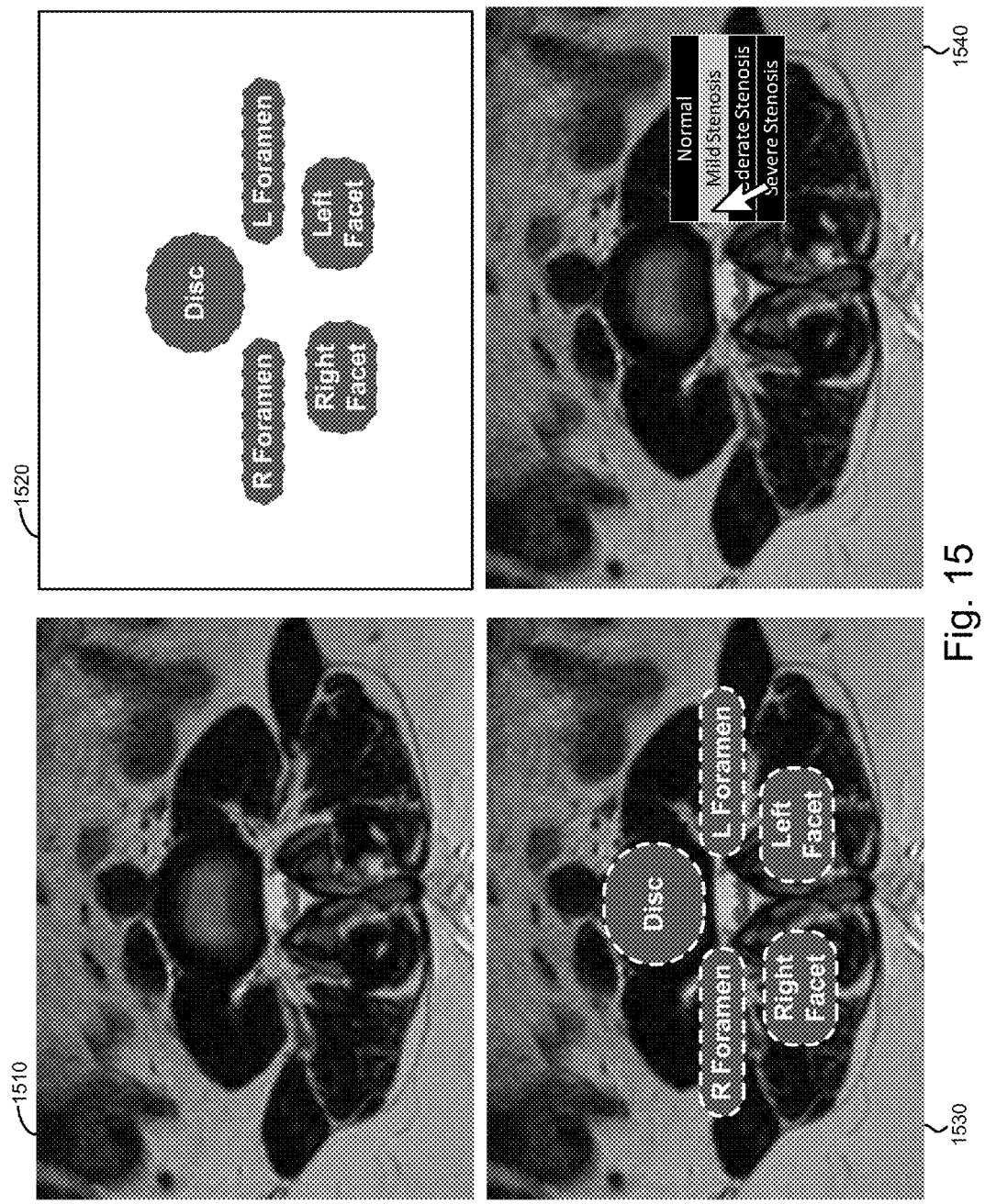
FIG. 15 illustrates an image frame and a report panel including a child report that corresponds to the image displayed in the image frame.

In some embodiments there is a linkage between contents of image frames and anatomic regions represented in reporting frames such the spatial and/or anatomic positions in image frames and reporting frames are linked. For example, in the embodiment described with reference to FIG. 5b, the system is aware of the anatomic levels represented in the images, e.g., L3-4 in image frame 534a, L4-5 in image frame 534b. Embodiments described with respect to FIGS. 14 and 15 are other examples where there is a spatial correlation between images and child reports. There are a number of manual or automatic methods that could be used to define and/or cross register anatomic positions within images to corresponding regions within one or more child report.

Figure 6B:
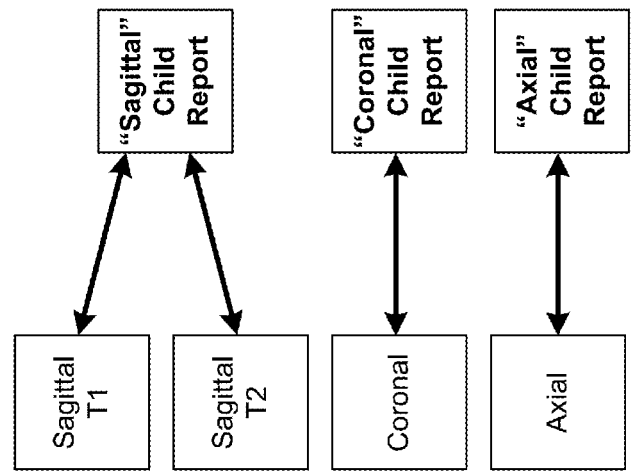
FIG. 6b is a block diagram illustrating an example of matching of image series and child reports for a lumber spine MRI.
Figure 6A:
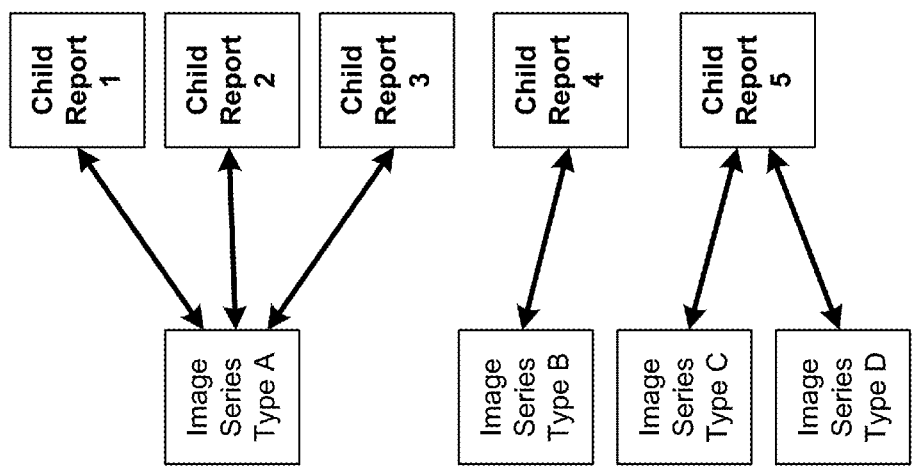
FIG. 6a is a block diagram illustrating example linkages between child report types and image series.

FIG. 6a is a block diagram illustrating example linkages between child report types and image series. In various embodiments, child reports may be matched and/or linked to various image series within medical imaging exams.

Rules for matching child reports may vary based on image type, image series type, and/or any other characteristics of medical data. Such rules may be stored in a data structure and may be based, for example on user preferences, site configurations, or default configurations. Matching of series type may also be based on one or more of a variety of factors, such as exam modality, exam description, clinical indication, clinical history, etc. Matching of image series types to child report types may also be interactively set and changed by the user. Information used for matching may include information such as the information available in a standard DICOM header of images or other information related to the exam and/or imaging series that may available in systems such as PACS, EMR, RIS, etc.

As illustrated in FIG. 6a, the matching of image series type to child reports may be one-to-one, one-to-many, or a many-to-one relationship. In particular, in the embodiment of FIG. 6a, image series type A is linked to three different child reports, child report 1, child report 2, and child report 3, while image series type B is linked to only a single child report 4. As noted above, a child report may be linked to multiple image series, such that changes to multiple image series cause updates to the child reports. In the example of FIG. 6a, child report 5 is linked to both image series type C and image series type D. In some embodiments, the linkages illustrated in FIG. 6a, for example, are used to select child reports that are displayed to a user in response to selection of an image series for display. For example, in response to a user selecting an image series of type A, a report processor may automatically select three child reports (child report 1, child report 2, and child report 3) for display to the user.

FIG. 6b is a block diagram illustrating an example of matching of image series and child reports for a lumber spine MRI. In this example, the Sagittal T1 and Sagittal T2 series types are matched with a "Sagittal" Child Report, such as the one shown in report panel 530a of FIG. 5b. Series obtained in the Coronal plane are matched to a "Coronal" Child Report. Series obtained in the Axial plane are matched to the "Axial" Child Report.

For the purposes of discussion, this is an example of association rules that associate series and/or image types with child reports.

As will be subsequently discussed, various exams may be matched to various reports, each of which may include one or more child reports.

Figure 7A:
FIG. 7a depicts a sample data structure storing associations between cardiac ultrasound views, which are analogous to "series" discussed herein, and child reports for a particular cardiac ultrasound report.

FIG. 7a depicts a sample data structure 700 storing association rules between cardiac ultrasound views, which are analogous to "series" discussed herein, and child reports for a particular cardiac ultrasound report.

Multiple cardiac ultrasound reports may be present, including parent reports and optional child reports, for example stored in report template data structure 166 (FIG. 1). The particular report(s) presented to the user for use may be determined by a variety of factors, such as, user preference (for example stored in user preferences data structure 164), exam type, modality, exam description, clinical indication, etc.

Based on such association rules, each cardiac child report, e.g., PLAX, PSAX, A4C, A2C, may be automatically associated with one or more series types in the exam, wherein the series type may be determined by extracting information from image DICOM headers to identify the cardiac view, for example. Thus, the computing device 150 executing the report processor for cardiac reports may automatically select for display a child report that matches a determined cardiac ultrasound view of a selected image, based on associations stored in a data structure, such as data structure 700.

Figure 7B:
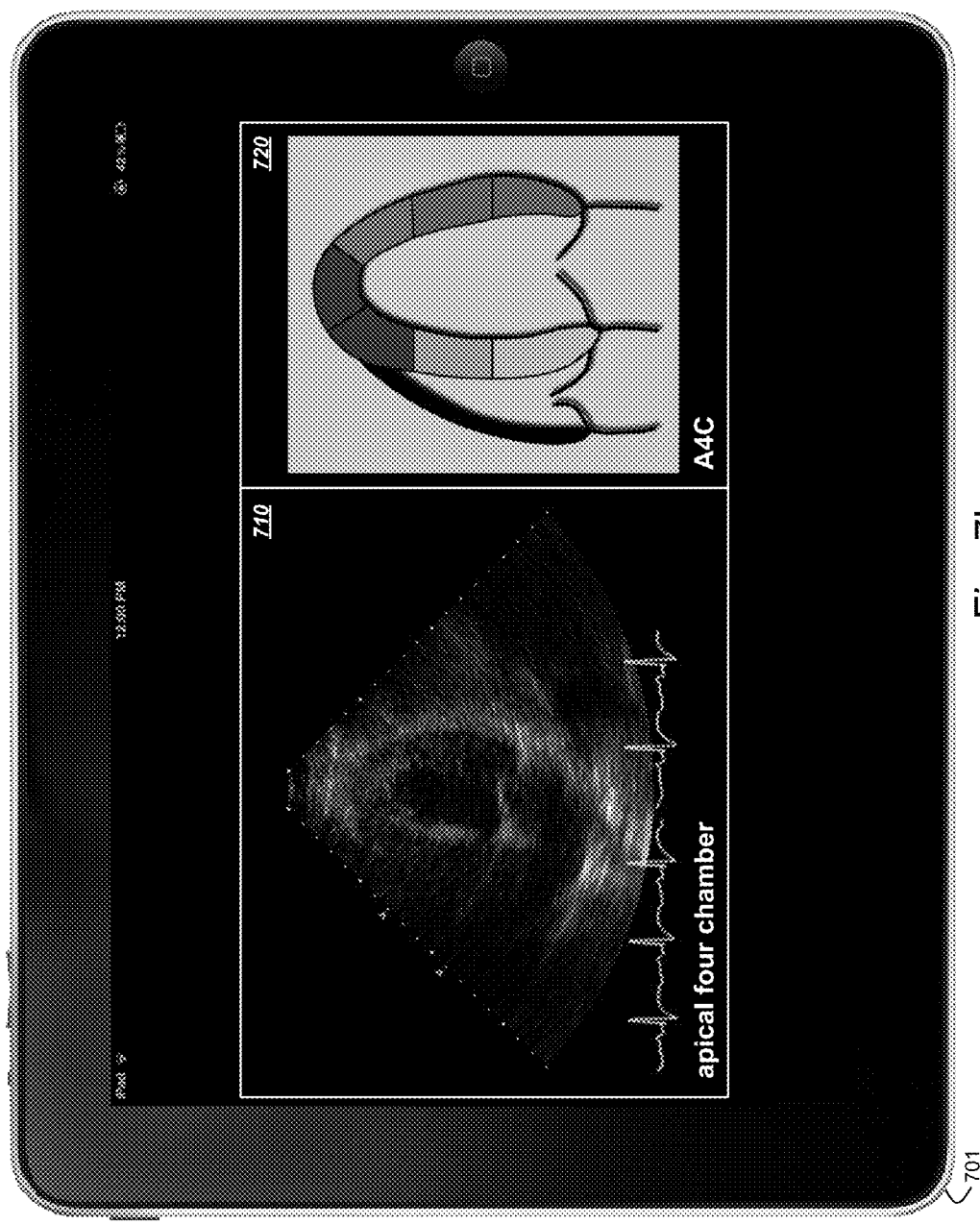
FIG. 7b illustrates a computing device that includes a display device depicting report panel and image frame.

FIG. 7b illustrates a computing device 701 that includes a display device depicting report panel 720 and image frame 710. The example computing device illustrated is a tablet computer that includes a touch screen, but other types of computing devices, display devices, and input devices could be utilized. Various computing devices, including tablets and mobile devices, as well as desktop computing system, may execute versions of the report processor software in order to provide one or more advantages discussed herein.

In this example, image frame 710 is displayed adjacent to report panel 720 on the computing device 701. Based on systems and methods described herein, the image frame 710 and report panel 720 are linked so that the child report displayed in the report panel 720 is automatically determined based on the image series displayed in the image frame 710.

In the example shown, the image frame 710 displays an apical four chamber view from a cardiac ultrasound exam. FIG. 7a shows the series-report association rules indicating that the "apical four chamber" image series is associated with the "A4C" child report. In this embodiment, the A4C child report depicted in report panel 720 is automatically selected by a report processor (e.g., executing on the computing device 701 or some other networked computing system) in response to determining that the image selected for viewing is in the apical four chamber image series.

If the user changes the image series displayed in the image frame 710, the child report shown in the report panel 720 is automatically changed based on the image-report association rules (e.g., stored in data structure 700 of FIG. 7a).

In other embodiments, multiple image frames and/or report panels may be simultaneously displayed, with linking of individual image frames and report panels, for example, based on hanging protocols or rules based on the physical proximity of the image frame to the report panels.

Figure 8:
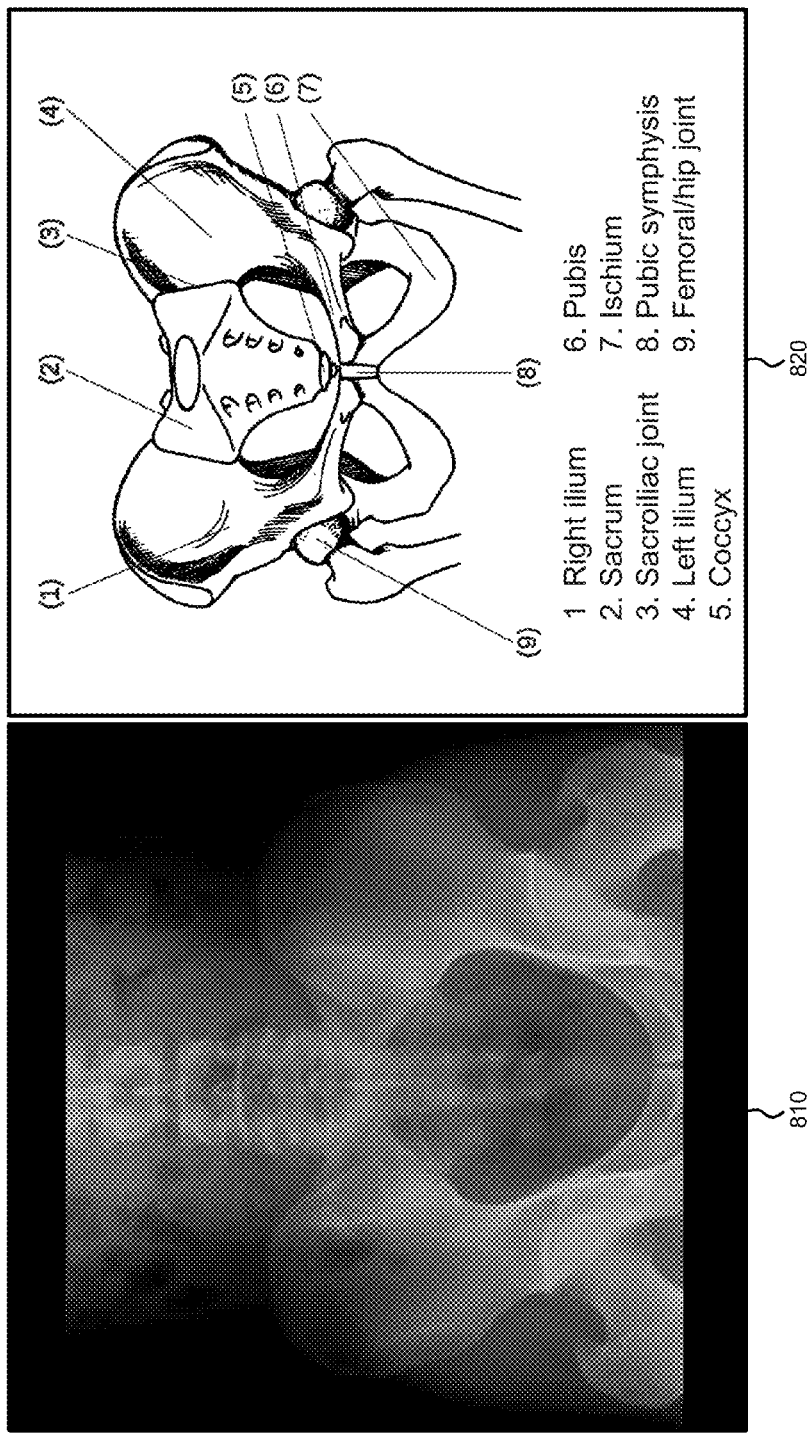
FIG. 8 illustrates an image frame and report panel where the child report shown is informational.

FIG. 8 illustrates an image frame 810 and report panel 820 where the child report shown in report panel 820 is informational. For example, the material presented could be material designed to support clinical decision making that could be in a variety of forms, such as text, images, and/or graphics, rather than to receive input from the user that may be included in a parent report. In some embodiments, one or more informational child reports may be shown concurrently with one or more child reports that are configured to receive input from a user that may be stored in a data structure (e.g., data structure 432 of FIG. 4b) and/or used in one or more other child reports or a parent report.

In the example shown, image frame 810 displays a radiograph of a pelvis and report panel 820 displays a diagram of the pelvis with various structures labeled.

Image-report association rules may include child reports that include educational, reference and/or material designed to support the decision making. Thus, relevant informational child reports may be automatically selected and displayed in response to display of a particular image, image type, series type or exam type in an image frame. For example, for imaging of the neck with CT or MRI, image-report association rules may include reference diagrams showing the nomenclature of lymph node level and/or drawings illustrating the anatomy of the neck.

Figure 9:
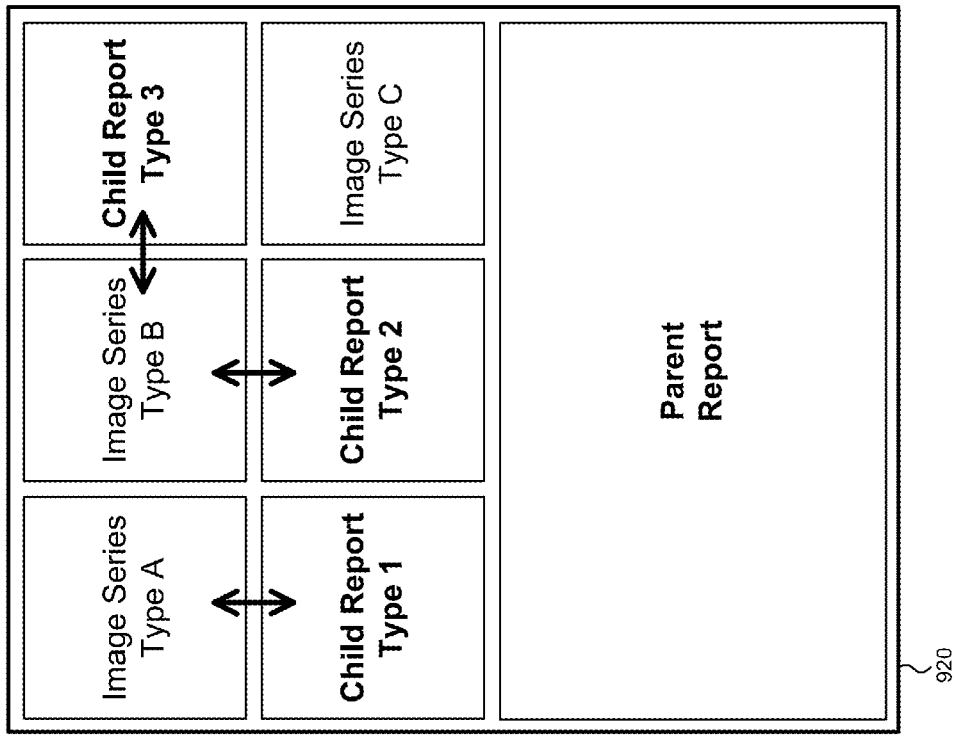
FIG. 9 illustrates example image-report hanging protocols that map layouts and/or content of image frames and report panels.
Figure 9:
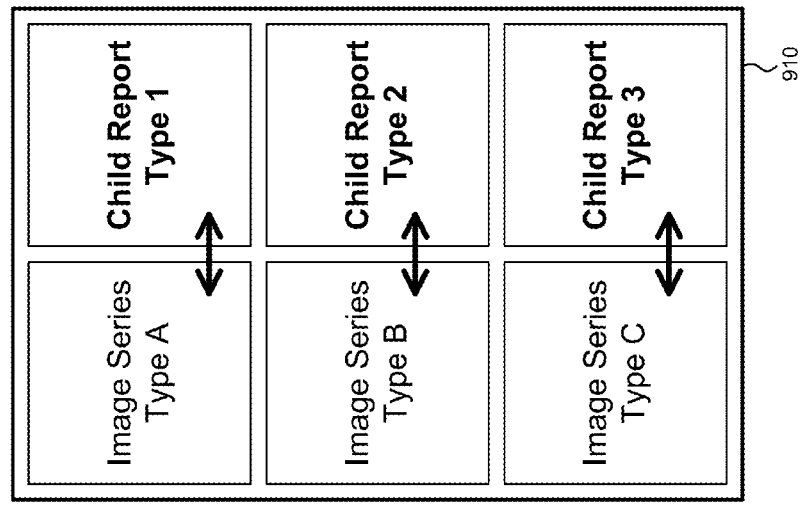

FIG. 9 illustrates example image-report hanging protocols 910 and 920 that map layouts and/or content of image frames and report panels. Image-report hanging protocols may have one or more of the following features:

- Map layout and/or content of image frames and report panels.
- Map linkage between image frames and report panels, as described herein.
- Defined by the user, for example stored in user preference data structure 164 or report template database or data structure 166, defined by the site, and/or default values.
- Apply to any display size and any number of displays.
- Apply to one or more characteristics of imaging exams, such as modality, exam type, exam description, clinical indication, patient history, etc.

In one embodiment, image-report hanging protocols map the linkage between image frames and report panels. This is illustrated as double headed arrows connecting image frames and report panels in the example hanging protocols 910 and 920. This linkage may define the behavior of a linked image frame and report panel, as described herein. For example, changing the content of an image frame may result in an automatic change in the linked report panel. In another embodiment, changing a report panel may result in an automatic change in the associated image frame.

The example image-report hanging protocol 910 shows a three row, two column layout, with the left column comprising three image frames containing the listed series types and the right column comprising three report panels containing the associated child report types. The double headed arrows linking image series type A to child report type 1, image series type B to child report type 2, and image series type C to child report type 3, indicates a linkage between the respective image frames and child report types.

The example image-report hanging protocol 920 illustrates a different layout and includes a panel for the parent report.

In some embodiments, hanging protocols may include layout and/or content of image frames and/or report panels for multiple display devices of a multi-display computing system. For example, different hanging protocols may indicate the layout and content of the image frames and report panels illustrated in FIGS. 2a-2d. In one embodiment, report packages are associated with respective hanging protocols, such that the report packages not only indicate the parent report and child reports that are selected for use by the user, but also indicate an initial organization of the parent reports and child reports as defined in the respective hanging protocol.

FIG. 10 illustrates image frames 1010 and 1020, report panels 1030 and 1040, and a parent report panel 1050. In this example, the medical exam displayed is a lumber spine MRI. The image frames and report panels are arranged and linked according to an image-report hanging protocol similar to hanging protocol 920 in FIG. 9, except that the "Child Report Type 3" report panel and "Image Series Type C" image frame are not present and the remaining image frames and panels are of a different size.

Image frames 1010 and 1020 display image series from a medical imaging exam. One image from each series is shown. Based on user interactions, the user may provide input to the system to display a different image from the series displayed within an image frame. For example, the user could position the cursor over an image frame and roll a mouse wheel to display the various images within an image series.

In the example shown, image frame 1010 displays one of the images from a sagittal T2 series and image frame 1020 displays one of the images from an axial T2 series, but the number and arrangement of frames used to display images may vary.

Report panels 1030 and 1040 are linked to image frames 1010 and 1020, respectively. Thus, the child reports that are displayed in the report panels 1030 and 1040 may be automatically selected or updated by the computing device in response to changing the image and/or image series displayed in the image frames 1010 and 1020, respectively.

In other embodiments, the number and arrangements of image frames and report panels may vary.

Figure 11:
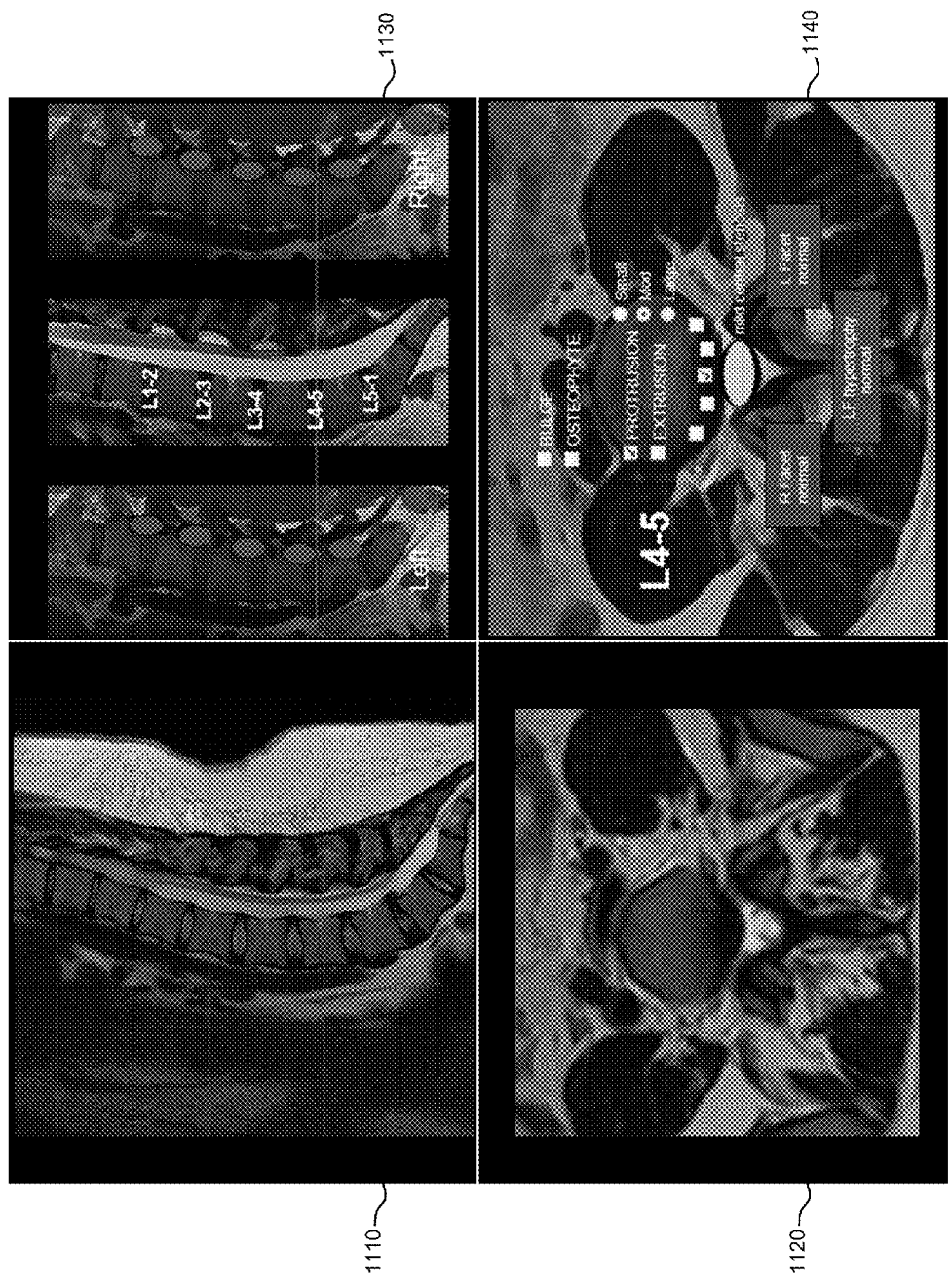
FIG. 11 illustrates four regions, any of which may contain an image or report component that are automatically determined by the arrangement and/or content of image frames.

FIG. 11 illustrates four regions, 1110, 1120, 1130, and 1140, any of which may contain an image or report component that are automatically determined by the arrangement and/or content of image frames. For example, a region of a computer display may contain a report panel or image frame that may be changed automatically or in response to user input. If a region contains a report, it will be described herein as a report panel. If it contains an image, it will be described as an image frame. In one embodiment, a user may change the content of a screen region, for example by choosing an image series to display from a list of available image series from the exam or exams that are available to his computing device. In response to displaying a series in a screen location on the computing device, in one embodiment, the associated linked child report may be automatically displayed, for example based on image-report association rules.

In one embodiment, a user may change the content of a screen region, for example by choosing a child Report to display from a list of available child reports. In response to displaying a child report in a screen location on the computing device, in one embodiment the associated linked image series may be automatically displayed, for example based on image-report association rules.

FIG. 12a illustrates an example image report hanging protocol 1210 that defines the layout of an image frame 1212 and child report panel 1214, but in this embodiment does not define the image series to be displayed in the image frame 1212. In other embodiments, the number, size and/or arrangement of image frames and report panels may vary. The double headed arrow linking the image frame 1212 and child report panel 1214 indicates that the two are linked.

Figure 12C:
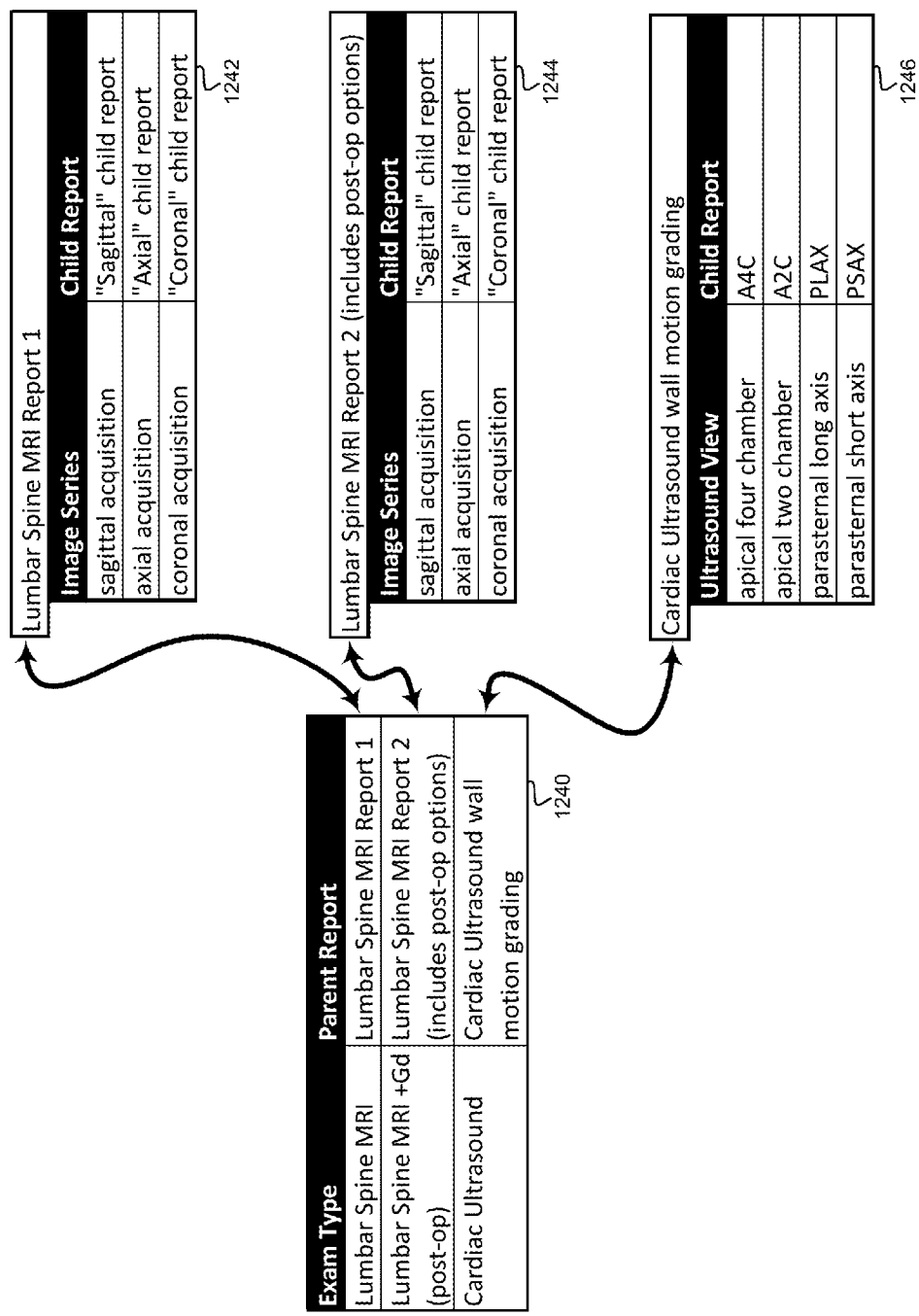
FIG. 12c illustrates example exam type to parent report rules that associates exam types to parent report templates and one or more child reports.

FIG. 12c illustrates example exam type to parent report rules 1240 that associates exam types to parent report templates and one or more child reports. In one embodiment, in response to selection of an exam for display a report package including a parent report and one or more child reports is selected (e.g., based on exam type and/or other exam characteristic). For example, with reference to FIG. 12c, in response to selection of a lumbar spine MRI, a report package including Lumbar Spine MRI Report 1, as well as each of the "Sagittal" child report, "Axial" child report, and "Coronal" child report, may be selected.

In the embodiment of FIG. 12c, each parent report template has additional rules, such as the rules 1242, 1244 and 1246 illustrated in FIG. 12c, for selecting when the respective child reports of the selected report package are displayed, based on a currently selected image series. Depending on the embodiment, rules 1240, 1242, 1246 may be stored in user preference data structure 164, report template data structure 166, or any other data structure.

In the examples of rules 1242 and 1244, a characteristic of each image series is utilized to match to a child report. In this example, the plane of acquisition of the series is used to determine the child report to be included in a particular report panel. In other embodiments, one or more other characteristics may be used, such as the pulse sequence for MRI, slice thickness for CT, the use of IV contrast, whether the series is the primary exam being read or a comparison exam, etc.

Returning to FIG. 12b, display screen 1220 is an example display based on image report hanging protocol 1210 and image-report association rules 1242 (wherein rules 1242 are selected based on the exam type and/or parent report). In this example of display screen 1220, the image frame (left) displays an image from the sagittal T2 series of a lumber spine MRI. The choice of that particular series from the available series may have been made by the user or based on other functionality within the system, such as user preferences or default settings. In addition, the particular image displayed from within the series could be based on other functionality within the system, such as user preferences or default settings, or the choice may have been made by the user interactively.

Once an image series is chosen for display in the image frame, based on systems and methods described herein, a child report is automatically displayed in the right panel, where the particular child report displayed is based on various rules, for example the ones illustrated FIG. 12c. For example, when the sagittal T2 series of a lumbar spine MRI is selected for display, the computing system applies the example rules 1242 (because the report package including the child reports associated with the Lumbar Spine MRI Report 1 were already selected based on one or more exam characteristics) of FIG. 12b and selects the "Sagittal" child report for display. Similarly, when the user then selects a coronal series of the exam for display, the rules 1242 are again applied to determine that the "Coronal" child report should be displayed, such as by replacing the currently displayed child report (e.g., the "Sagittal" child report), or displaying a new report panel including the "Coronal" child report.

Display 1230 displays the appearance of the image frame and report panel after the user has changed the content of the image frame on the left to an axial T2 series. A variety of interactions could be used to cause the computing device to change the series displayed in the image frame, e.g., interaction with a computer keyboard, mouse, touchscreen, or other input device. Based on systems and methods described herein, changing the image series displayed automatically causes the child report displayed in the right panel to change. In the example shown, a "Lumbar Spine MRI", the parent report chosen on the basis of association rules 1240 (e.g., exam-report association rules) is the "Lumbar Spine MRI Report 1". The association rules 1242 associated with that parent report indicate a match between images acquired in the axial plane ("axial acquisition") like the one shown in the image frame of computer display 1230, and the "Axial" Child Report. Therefore the "Axial" Child Report is shown in the right region, the report panel, of computer display 1230.

In some embodiments, the user may change the report panel displayed in the right frame and the system automatically changes the image series displayed in the left frame based on linking rules.

Figure 13:
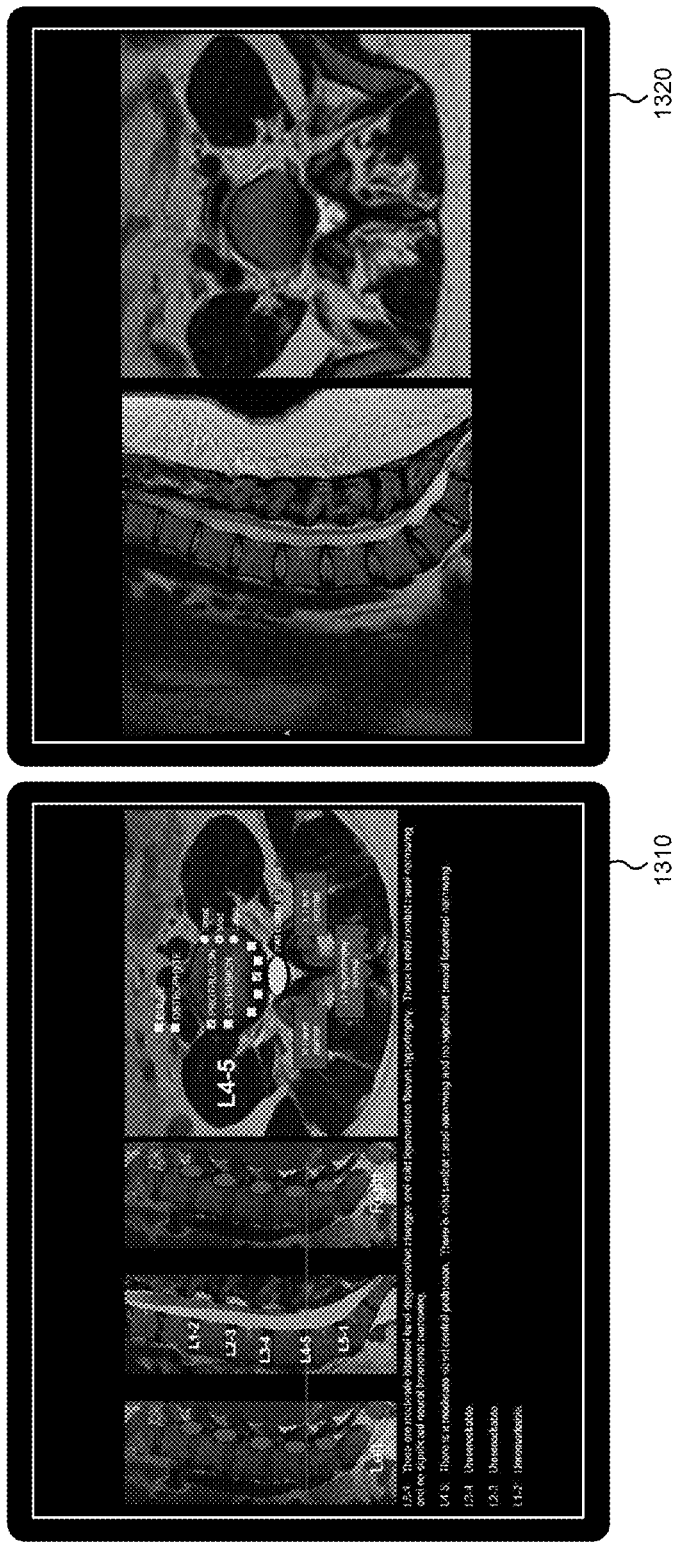
FIG. 13 illustrates display devices that display various portions of linked report panels and image frames.

FIG. 13 illustrates display devices 1310 and 1320 that display various portions of linked report panels and image frames. In the example shown, display device 1310 displays a parent report below two child reports, and is used for the reporting system. Display device 1320 displays two image frames that include images, such as from an image management system, such as a PACS system.

A configuration that includes report panels and image frames on different displays and/or computing devices may be useful in cases where the image display device(s) may be interfaced to the PACS system, for example, and the image display device(s) used for reporting, are controlled by separate computing devices. For example, the PACS system and reporting system may be running on separate computers where the display devices are in proximity. In some embodiments one or both systems may be mobile devices, such as tablet computers or smartphones.

FIG. 14 illustrates image frames 1410 and 1420 with a report panel superimposed in different manners. As noted above, a report panel may be positioned in various locations of a display, such as next to one or more image frames or other report panels. In some embodiments, report panels may be superimposed on one or more image frames and or report panels. In the embodiment of FIG. 14, report panel 1412 is superimposed on the image frame, which depicts an apical four chamber view of a cardiac ultrasound. In this embodiment, the report panel 1412 displays a child report that is associated with the displayed image. In one embodiment, the child report displayed in the report panel 1412 was automatically selected by the report processor, such as based on rules similar to those discussed above. The position of a report panel relative to an image may be determined in a number of ways, including but not limited to, determined automatically, set as a default, set as a user preference, or determined in response to user interactions.

In another embodiment, a report panel may be superimposed on an image so that specific features within the child report are superimposed on certain features within the images (e.g., corresponding features). For example, the child report may be resized and/or rotated and/or morphed to superimpose on the structure of interest. These operations may be done manually or automatically.

In addition, a report frame may be displayed as translucent (or various user-definable levels of opacity) so that the report panel and the image, including the image below the report panel, may be viewed simultaneously. These features are illustrated in view 1402 where the report panel 1412 has been morphed and superimposed on the left ventricle of an image series from a cardiac ultrasound. The user may make the report panel invisible so that it does not obscure his observation of the features of the image, yet still interact with the child report by, for example, clicking on various regions. In one embodiment, the user may toggle the report frame on and off, making it visible or invisible, for example with input from a mouse, keyboard, voice command, touchscreen, or other input device.

FIG. 15 illustrates an image frame 1510 and a report panel 1520 including a child report that corresponds to the image displayed in the image frame 1510. While the image frame 1510 and report panel 1520 may be viewed side-by-side as shown in FIG. 15 (or in any other arrangement), in other embodiments, the report panel 1520 may be superimposed on the image frame and rendered invisible so that is does not interfere with visualization of the underlying image, while retaining functionality associated with portions of the child report included in the report panel 1520.

In the embodiment of FIG. 15, the image in image frame 1510 is an example axial T2 weighted image from a lumber spine MRI and the child report in report panel 1520 includes five regions that the user can interact with, labeled "Disk", "R Foramen", "L Foramen", "Right Facet", and "Left Facet". In one embodiment, the report panel 1520 is superimposed on the image frame 1510, possibly after automatic or manual registration of the child report with the image, and made invisible so that the user sees does not see the superimposed report panel 1520. For example, image frame 1530 is shown with the report panel 1520 superimposed on the image frame 1530. As noted above, the report panel could be rendered invisible so that the original image, for example, 1510 is not compromised. In other embodiments, the report panel may be made visible in response to a user action. In some embodiments, the report panel may be resized and/or rotated and/or morphed to better fit the structures of interest within the image. While the report panel may be rendered invisible, the user can still interact with it as illustrated in FIG. 15.

While the report panel may be invisible, it may still be responsive to user action. In the example of image frame 1540 (which includes report panel 1520 superimposed on the image, but made invisible), the user positioned the cursor into the region corresponding to the "L foramen" of the report panel 1520. By clicking into the region, the child report displays the list of options, and in the example shown the user selected "Mild Stenosis". In other embodiments, other forms of user interaction may be used, for example involving a mouse, trackball, keyboard, touchpad, touchscreen, etc.

Figure 16:
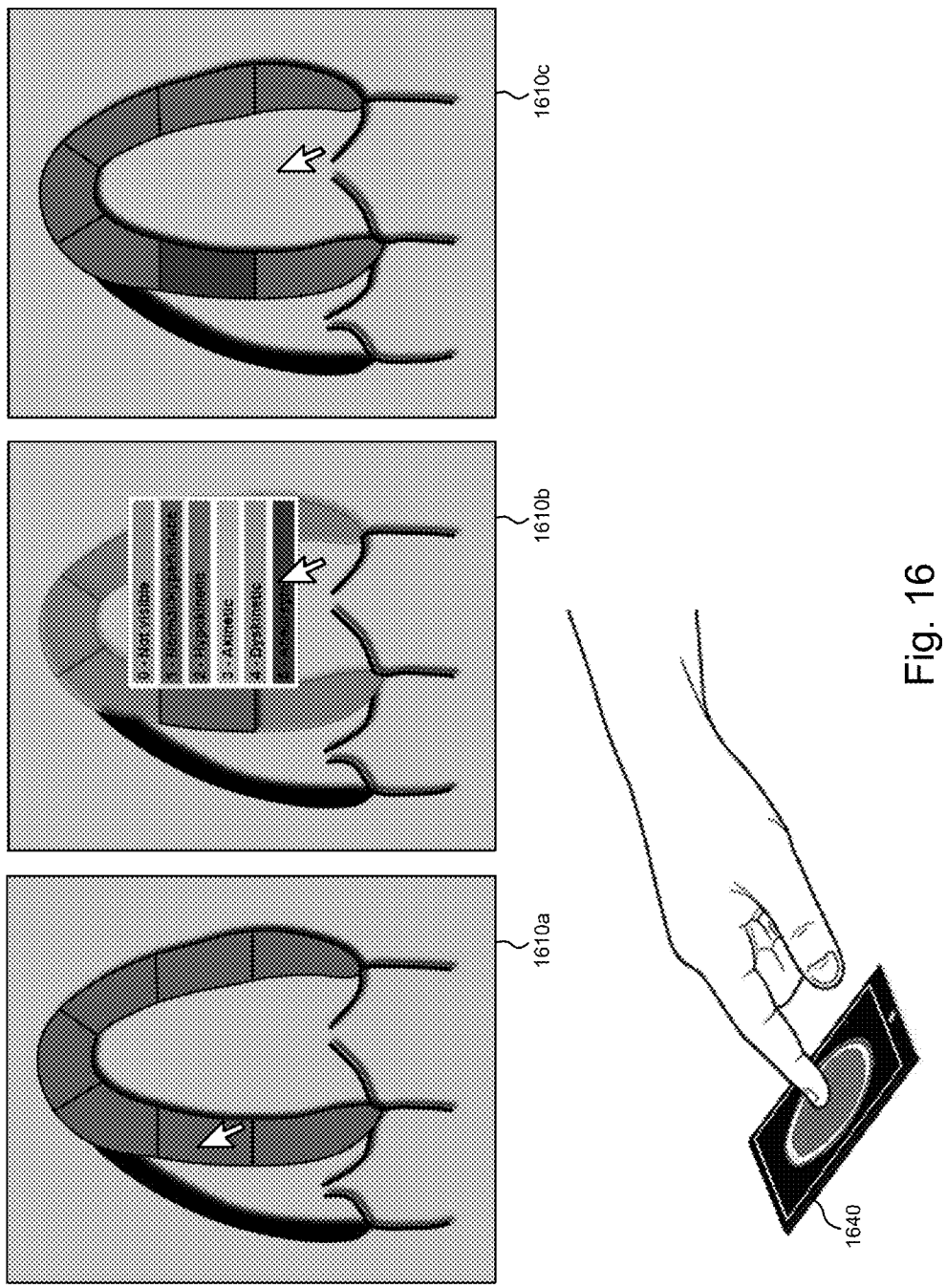
FIG. 16 illustrates a report panel as a user interacts with a child report displayed in the report panel.

FIG. 16 illustrates a report panel 1610 as a user interacts with a child report displayed in the report panel 1610. Thus, report panel 1610a, 1610b, and 1610c show the same report panel with changes made to the child report over time.

In report panel 1610a, the user has positioned a cursor over a region of the child report that is responsive to user action. This example shows an apical four chamber view of the heart where there are 7 heart wall regions that the user can grade, the 7 green regions outlined by black lines. In the example of report panel 1610a, the cursor is positioned over the "Mid Inferoseptum" wall segment.

In response to the user selecting the "Mid Inferoseptum" wall segment, the report panel 1610b lists options that may be selected. In the example of FIG. 16, the user has positioned the cursor over "5—Aneurysm" to choose that option and clicked a mouse button. In response to selection of "5—Aneurysm," the report panel 1610c indicates the grading and color of that wall segment.

In other embodiments, other forms of user interaction may be employed, for example using a touchscreen device 1640, or rolling a mouse wheel while a cursor is positioned over a wall segment.

Figure 17:
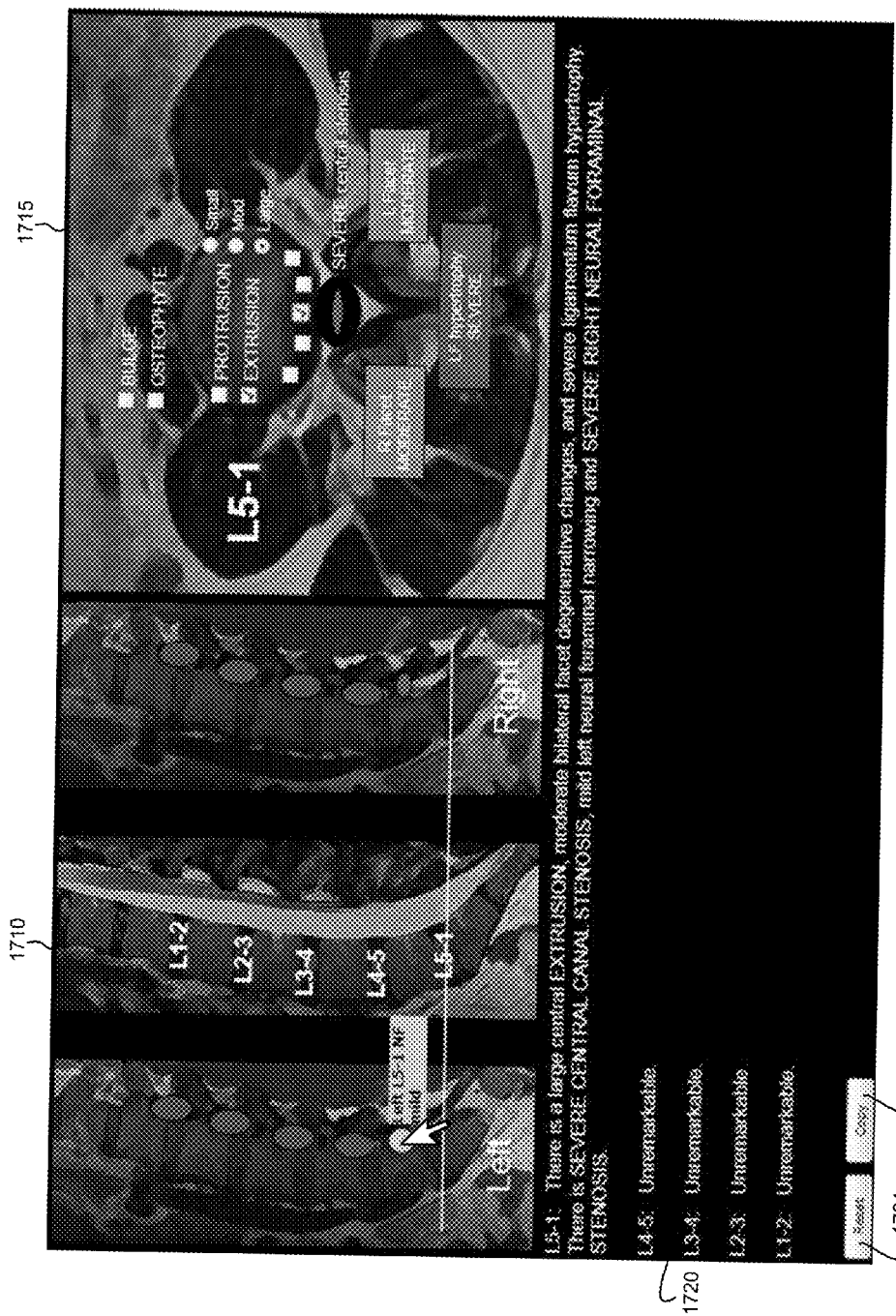
FIG. 17 illustrates a sample layout of report panels including two child report panels and a report panel that includes a "Reset" button and a "Copy" button.

FIG. 17 illustrates a sample layout of report panels including child report panels 1710 and 1715, and report panel 1720 that includes a "Reset" button 1721 and a "Copy" button 1722. In this embodiment, moving a cursor over (or touching on a touchscreen device) a structure responsive to user input may result in automatic display of the current "rating" or other information related to that structure. In the example of child report panel 1710, there are 10 oval regions corresponding to the neural foramina in the lumbar spine diagram. In the example shown, the cursor has been placed over the left L5-1 neural foramen and a pop-up display reports the anatomic region and current rating, "Left L5-1 NF" and "mild" stenosis, respectively.

In the embodiment shown, the user may change the "rating", e.g., the degree of stenosis, of a neural foramen by positioning the cursor over a structure in the child report and rolling the mouse wheel forward or backward to change among the stored ratings: normal, mild, moderate, and severe stenosis. In response to changing the rating of a structure, the color, shape, size and/or other characteristic of the structure may change. In other embodiments, one or more of color, size, shape, and/or text description may change.

Other structures that may be manipulated in similar ways are shown in child report panel 1715. In the example of child report panel 1715, other forms of user input are utilized, for example the check boxes and radio buttons shown.

Example "Reset" button 1721 may be used to reset the child reports and parent report to its default state. Example "Copy" button 1722 may be used to copy the text within the parent report (in report panel 1720) that was automatically generated in response to the user manipulating the graphically based child report panels. This text may then be pasted into another system, such as radiology information system.

FIG. 18 is a flowchart illustrating one embodiment of a method of generating a parent report (e.g., a textual report describing findings in a series of medical images) based on data received from a user via one or more child reports (e.g., graphical user interfaces with control that allow the viewer to intuitively provide findings regarding medical images). Depending on the embodiment, the method of FIG. 18 may include fewer or additional blocks and/or the blocks may be performed in a different order than is illustrated. Software code configured for execution on a computing device in order to perform the method of FIG. 18, such as report processor software discussed above, may be provided on a computer readable medium, such as a compact disc, digital video disc, flash drive, hard drive, memory device or any other tangible medium. Such software code may be stored, partially or fully, on a memory of a computing device, such as the computing device 150, and/or other computing devices illustrated in the Figures, in order to perform the method outlined in FIG. 18 by those respective devices. For ease of explanation, the method will be described herein as performed by a computing device, which should be interpreted to include any one or more of the computing devices noted above and/or any other suitable computing device.

Beginning in block 1810, the computing device receives a selection of an exam for display to the user. Depending on the embodiment, the exam may be selected by the user (such as from a list of image series that are available for viewing by the user) and/or automatically (such as based on user preference for selection of image series to view).

Next, in block 1820, the computing devices accesses one or more sets of rules in order to determine a report package, including a parent report and at least one child report, that are associated with the selected exam. In one embodiment, the rules comprise associations between respective exam types (and/or other exam characteristics) and one or more report packages (e.g., combinations of child reports and/or parent reports). For example, a first exam type may be associated with 3 different child reports and a single parent report, while a second series type may be associated with a single child report and a single parent report. In one embodiment, the child reports are at least partially graphical so that the user can provide data regarding medical images in an intuitive manner.

Moving to block 1830, the computing device displays at least some of the one or more reports selected in block 1820. Depending on the embodiment, all child reports may be concurrently displayed, a subset of the selected child reports may be concurrently displayed, or none of the child reports may be displayed (e.g., the reports may be hidden, but still operable to receive user input, and/or displayed in response to user input). For example, child reports may be alternatively displayed, such as in response to the user navigating between various images of an image series or providing other input. Similarly, the parent report may be hidden, selectively displayed, or concurrently displayed with one or more child reports while data is being received in the child reports. As noted above, in some embodiments at least some of the child reports are primarily graphical in nature such that data from the user (e.g., analysis of medical images) can be provided in an intuitive interface. In other embodiments, the child reports may be non-graphical (e.g., textual). Depending on the embodiment, the reports may be displayed in different locations (e.g., in fixed position report panels, floating report panels, resizable/rotatable/configurable report panels), with varying opacity levels, and/or with any other display parameter adjustment.

In block 1840, the computing device receives data from the user via one or more child reports. The data received via the child reports may be stored in a report data structure, such as the example data structure of FIG. 4b. Alternatively, the received data may be stored in any other data structure in any available format.

In block 1850, the parent report is generated and updated based on data received in the child reports. In one embodiment, the parent report is updated in real time as data is received in the child reports, even if the parent report isn't displayed to the user at the time of the updates. In an embodiment where the parent report is displayed and updated as data is received in the child report(s), the user may watch as textual (or graphical) updates are made to the parent report based on particular changes to data that is provided to the child reports. In other embodiments, the parent report is generated in response to a report generation trigger, such as a request from the user to view the parent report. In one embodiment, the parent report may be automatically transmitted to one or more other computing systems, such as a PACS, a referring doctor computing system, and/or a patient computing system. In this manner, the parent report may be quickly delivered to the appropriate parties, without requiring time for transcription of a dictated report as may currently be performed by a radiologist, for example.

Other

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer-implemented method comprising:
   receiving selection of an exam for display on one or more displays of a computing system having one or more computer processors, the exam including a plurality of image series, each of the plurality of image series being associated corresponding image series types;
   determining an exam characteristic associated with the exam;
   accessing a data structure storing an association between the exam characteristic and a report package, the report package comprising a parent report and one or more child reports, the data structure further storing associations between each of the one or more child reports and respective image series types;
   selecting from the data structure the report package, wherein the one or more child reports of the report package are configured to receive diagnosis data from a user of the computing system regarding one or more images of respective image series of respective image series types associated with the one or more child reports;
   identifying a first image series of the plurality of image series of the exam having a first image series type;
   identifying a first child report of the one or more child reports, wherein the first child report is associated with the first image series type;
   identifying features of interest in at least one image of the first image series;
   determining portions of the first child report corresponding to respective features of interest in the at least one image;
   displaying, on the one or more displays, the parent report, the first child report, and the at least one image; and
   at least partially superimposing the portions of the first child report on respective corresponding features of interest in the displayed at least one image of the first image series.

2. The computer-implemented method of claim 1, wherein the portions of the first child report that are at least partially superimposed on the respective corresponding features of interest in the displayed at least one image of the first image series are at least partially transparent.

3. The computer-implemented method of claim 1 further comprising:
   automatically analyzing the at least one image of the first image series to automatically identify the one or more features of interest in the at least one image.

4. The computer-implemented method of claim 1 further comprising:
   automatically analyzing the first child report to automatically identify important findings in the first child report.

5. The computer-implemented method of claim 4 further comprising:
   automatically emphasizing the important findings identified in the first child report.

6. The computer-implemented method of claim 5, wherein automatically emphasizing comprises at least one or highlighting, capitalizing, bolding, or coloring.

7. The computer-implemented method of claim 1, wherein the first child report is at least partially graphical so that the user can provide input in an intuitive manner by selecting portions of the first child report associated with graphical anatomical structures.

8. The computer-implemented method of claim 1 further comprising:
   in response to receiving diagnosis data from the user of the computing system to the first child report, automatically updating the parent report with similar diagnosis data.

9. The computer-implemented method of claim 1 further comprising:
   in response to receiving diagnosis data from the user of the computing system to the at least one image of the first image series, automatically updating the first child report with similar diagnosis data.

10. The computer-implemented method of claim 1, wherein the exam characteristic comprises at least one of: an exam type, an exam modality, a clinical indication and/or other clinical information, a medical history of a patient, or risk factors associated with the patient.

11. A computing system comprising:
    a data structure storing an association between the exam characteristic and a report package, the report package comprising a parent report and one or more child reports, the data structure further storing associations between each of the one or more child reports and respective image series types;
one or more displays; and
one or more computer processors configured with computer-executable instructions in order to:
  receive selection of an exam for display on the one or more displays, the exam including a plurality of image series, each of the plurality of image series being associated corresponding image series types;
  determine an exam characteristic associated with the exam;
  select from the data structure the report package, wherein the one or more child reports of the report package are configured to receive diagnosis data from a user of the computing system regarding one or more images of respective image series of respective image series types associated with the one or more child reports;
  identify a first image series of the plurality of image series of the exam having a first image series type;
  identify a first child report of the one or more child reports, wherein the first child report is associated with the first image series type;
  identify features of interest in at least one image of the first image series;
  determine portions of the first child report corresponding to respective features of interest in the at least one image;
  display, on the one or more displays, the parent report, the first child report, and the at least one image; and
  at least partially superimpose the portions of the first child report on respective corresponding features of interest in the displayed at least one image of the first image series.

12. The computing system of claim 11, wherein the portions of the first child report that are at least partially superimposed on the respective corresponding features of interest in the displayed at least one image of the first image series are at least partially transparent.

13. The computing system of claim 11, wherein the one or more computer processors are further configured with computer-executable instructions in order to:
  automatically analyze the at least one image of the first image series to automatically identify the one or more features of interest in the at least one image.

14. The computing system of claim 11, wherein the one or more computer processors are further configured with computer-executable instructions in order to:
  automatically analyze the first child report to automatically identify important findings in the first child report.

15. The computing system of claim 14, wherein the one or more computer processors are further configured with computer-executable instructions in order to:
  automatically emphasize the important findings identified in the first child report.

16. The computing system of claim 15, wherein automatically emphasizing comprises at least one or highlighting, capitalizing, bolding, or coloring.

17. A non-transitory computer-readable storage medium storing computer-executable instructions that, when executed by one or more computer processors, cause the one or more computer processors to:
  receive selection of an exam for display on one or more displays of a computing system, the exam including a plurality of image series, each of the plurality of image series being associated corresponding image series types;
  determine an exam characteristic associated with the exam;
  access a data structure storing an association between the exam characteristic and a report package, the report package comprising a parent report and one or more child reports, the data structure further storing associations between each of the one or more child reports and respective image series types;
  select from the data structure the report package, wherein the one or more child reports of the report package are configured to receive diagnosis data from a user of the computing system regarding one or more images of respective image series of respective image series types associated with the one or more child reports;
  identify a first image series of the plurality of image series of the exam having a first image series type;
  identify a first child report of the one or more child reports, wherein the first child report is associated with the first image series type;
  identify features of interest in at least one image of the first image series;
  determine portions of the first child report corresponding to respective features of interest in the at least one image;
  display, on the one or more displays, the parent report, the first child report, and the at least one image; and
  at least partially superimpose the portions of the first child report on respective corresponding features of interest in the displayed at least one image of the first image series.

18. The non-transitory computer-readable storage medium of claim 17, wherein the first child report is at least partially graphical so that the user can provide input in an intuitive manner by selecting portions of the first child report associated with graphical anatomical structures.

19. The non-transitory computer-readable storage medium of claim 17, wherein, when executed by one or more computer processors, the computer-executable instructions cause the one or more computer processors to further:
  in response to receiving diagnosis data from the user of the computing system to the first child report, automatically update the parent report with similar diagnosis data.

20. The non-transitory computer-readable storage medium of claim 17, wherein, when executed by one or more computer processors, the computer-executable instructions cause the one or more computer processors to further:
  in response to receiving diagnosis data from the user of the computing system to the at least one image of the first image series, automatically update the first child report with similar diagnosis data.

* * * * *